(12) United States Patent
He et al.

(10) Patent No.: US 7,098,034 B2
(45) Date of Patent: Aug. 29, 2006

(54) SYSTEMS AND METHODS FOR ASSESSING THE PRESENCE OF AND/OR THE LEVEL OF ANTI-STRIPPING CONSTITUENTS IN ASPHALT BINDERS OR ASPHALT MIXTURES

(75) Inventors: Tianqing He, Cary, NC (US); Ali Regimand, Raleigh, NC (US); Peter D. Muse, Durham, NC (US); Lawrence H. James, Raleigh, NC (US)

(73) Assignee: InstroTek, Inc., Raleigh, NC (US)

( * ) Notice: Subject to any disclaimer, the term of this patent is extended or adjusted under 35 U.S.C. 154(b) by 446 days.

(21) Appl. No.: 10/327,833

(22) Filed: Dec. 23, 2002

(65) Prior Publication Data

US 2004/0121473 A1     Jun. 24, 2004

(51) Int. Cl.
*G01N 33/24* (2006.01)
*G01N 21/00* (2006.01)

(52) U.S. Cl. .......................... 436/32; 436/28; 436/163; 436/164

(58) Field of Classification Search ...................... None
See application file for complete search history.

(56) References Cited

U.S. PATENT DOCUMENTS 5,306,343 A * 4/1994 Richardson et al. ........ 106/668

FOREIGN PATENT DOCUMENTS

DE      3937635 A1 * 5/1991
JP      01044834 A * 2/1989
JP      05288655 A * 11/1993

OTHER PUBLICATIONS

"Calcium Hydroxide" http://www.jtbaker.com/msds/englishhtml/C0407.htm.*
King et al. "Acid/base chemistry for asphalt modification", Asphalt pavong Technology, 2002, v. 71, pp. 147-175.*
Little et al. "Topic 2.Chemical and Mechanical Processes of Moisture Damage n Hot-Mix Asphalt Pavements", 2003.*
Maupin "Final Report. Quantitative determinaitn of asphalt antistripping additive", Jul. 2004, http://www.instrotek.com/stripscan.htm.*
Anderson et al., *Asphalt Binders*, A2D01:Committee on Characteristics of Bituminous Materials, Transportation in the New Millennium pp. 1-6. Date is unknown but is believed to be sometime in 2000, and the date for examination purposes is 2000.

(Continued)

*Primary Examiner*—Yelena G. Gakh
(74) *Attorney, Agent, or Firm*—Myers Bigel Sibley & Sajovec PA

(57) ABSTRACT

Methods, systems, and computer program products analyze asphalt samples for anti-stripping agents by: obtaining a sample comprising asphalt binder material; sensing a selected parameter associated with the sample (such as the acidity and/or alkalinity of the sample); and analyzing the sensed parameter to assess at least one of: (a) the presence of at least one anti-stripping agent in the sample; and (b) the level of at least one anti-stripping agent in the sample. The sample can be heated so that it emits exhaust gas and the exhaust gas (directly or indirectly) interrogated to determine its pH, or other constituents or properties, such as ammonia. Pre-defined mathematical relationships can be used to correlate the measured sensed data to the concentrations of the anti-stripping agent(s) in the sample undergoing analysis. The evaluation can be carried out in a generally automated rapid manner so that the test can be completed in about 10 minutes or less. Related devices and kits are also described.

42 Claims, 20 Drawing Sheets

OTHER PUBLICATIONS

Anderson, Dr. David A., *Manual of Practice for Conducting Superpave Asphalt Binder Tests*, Northeastern Superpave Center News, vol. 1, No. 3, pp. 1-2, Summer 1999.

Babcock, et al., *Study of Asphalt Binders using Lap Shear Bonds*, DuPont™ Elvaloy® RET, 10 sheets, http://www.dupont.com/asphalt/lapshear/lapshear.html. Date is unknown; however, it is copyrighted in 2002 and for examination purposes its date is prior to the filing date of the pending application.

Bahia, Dr. Hussain U., *Superpave Protocols for Modified Asphalt Binders*, http://www.utexas.edu/research/superpave/articles/bahia.html, 3 sheets, © 1996.

Braik, Osama Abdulwahab, *Stripping of Asphalt Mixtures and the Effectivenesss of Antistripping Additives*, http://www.environment.gov.jo/asphalt_stripping.htm, 1 sheet, 1987.

Button, Joe W., *Relationship Between Asphalt Interlayers and A. Asphalt Stripping, B.Bleeding or Rutting Pavements*, 2 sheets. Date is unknown, but it is believed to have been published during the early 1990's, and this date is to be used for examination purposes.

Lin et al., *Lifetime-Based pH Sensors: Indicators for Acidic Environments*, pp. 162-167, Oct. 29, 1998.

Nguyen et al., *Development of a Method for Measuring Water-Stripping Resistance of Asphalt/Siliceous Aggregate Mixtures*, NISTIR 5865, pp. i-vii and 1-42, Jul. 1996.

Stonex, Anne, *Northeast Asphalt User/Producer Group (NEAU/PG) and Pennsylvania DOT Implementation of Superpave in Pennsylvania*, pp. 11, Apr. 1999.

Yildirim, Yetkin, *Mixing and Compaction Temperatures for Modified Asphalt Binders*, http://www.utexas.edu/research/superpave/articles/yetkin2.html, 4 sheets, © 1996.

*Ocean Optics Sensors Group Delivers Innovative pH Optrodes*, Ocean Optics Inc., 2001, http://www.oceanoptics.com/corporate/Press%20Releases/pH%20Sensor_release.asp, 1 sheet, © 2001.

*pH Sensors*, http://www.thi-bailey.com/phsensor/phsensor.html, 2 sheets, © 1997-1999.

*SAMI-pH Sensor*, www.sunburstsensors.com/sami-ph.htm, 1 sheet, © (believed to be Oct.) 2002 and for examination Oct. 2002 is to be the date of this reference.

*Selection and Evaluation of Performance-Graded Asphalt Binders for Virginia*, VTRC 99-R21RB, 3 sheets, Jul. 1999.

Strategic Highway Research Program (SHRP), *SHRP Performance Graded Asphalt Binders*, 1987, http://www.bei-emulsions.com/shrp.htm 6 sheets, © —1996-1997.

\* cited by examiner

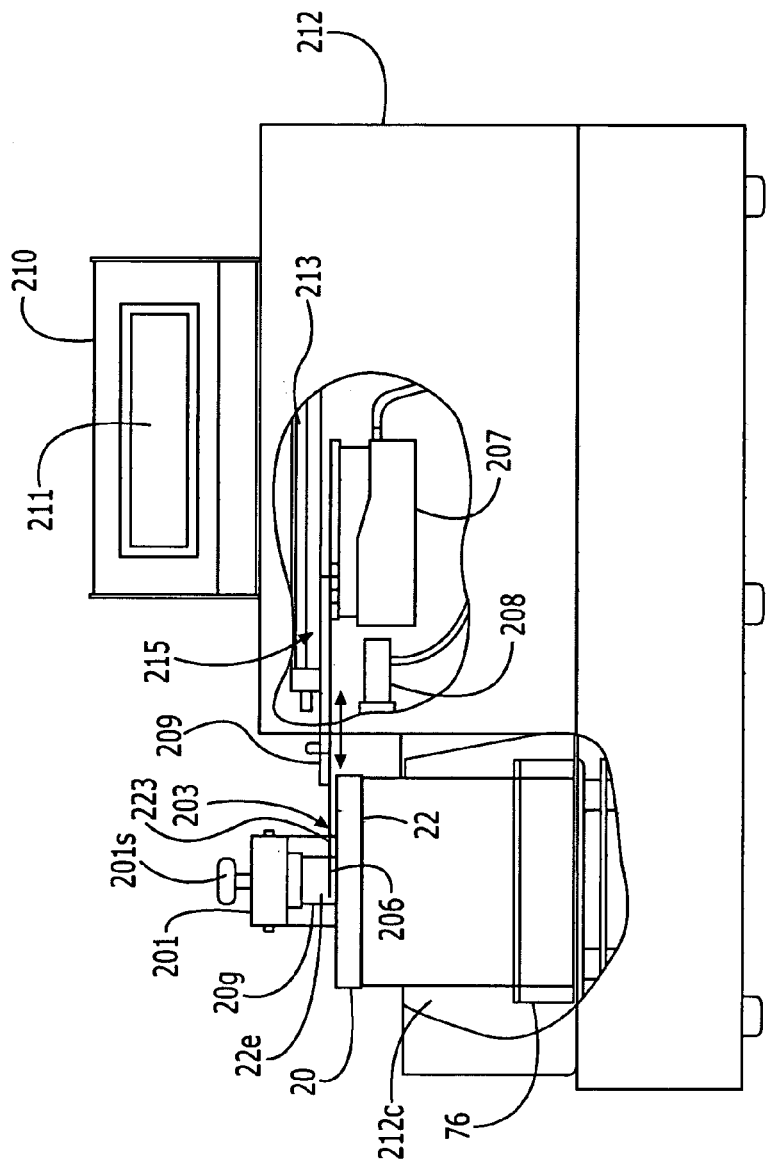
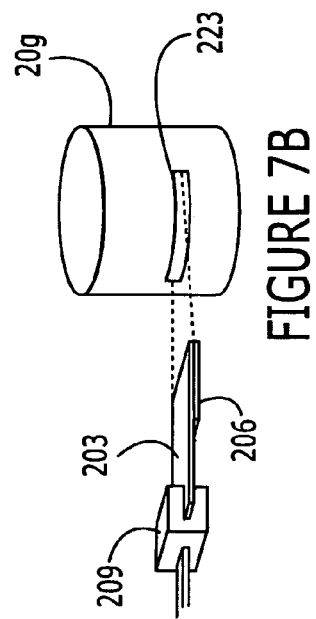
Parts of the StripScan
FIGURE 7A
FIGURE 7B

Loading the vapor trap
(left end view)

Loading the test strip test strip is moved inside the machine and pH paper is read before exposure to vapors Loading the sample to be tested. Photocell detects presence of sample, temperature probe is placed in sample, and sample heater controls sample temperature.

Vapor trap lowered onto sample container. Test strip is still inside the machine waiting for correct sample temperature. Positive fan pressure in cabinet prevents vapors from entering cabinet.

Sample reaches correct temperature. pH paper on test strip is moved inside vapor trap and over hole in sample container to be exposed to sample vapors pH paper on test strip is moved back into cabinet by slide and over the lens of the spectrophotometer. Spectrophotometer turns on and reads color.

SYSTEMS AND METHODS FOR ASSESSING THE PRESENCE OF AND/OR THE LEVEL OF ANTI-STRIPPING CONSTITUENTS IN ASPHALT BINDERS OR ASPHALT MIXTURES

FIELD OF THE INVENTION

This invention is related to methods and systems used to determine the presence and/or level of anti-stripping constituents in asphalt related materials, including asphalt binders and/or asphalt binders mixed with aggregate materials used in the construction of roads, pavements and the like.

BACKGROUND OF THE INVENTION

Asphalt pavements include asphalt binders combined with aggregates compacted to a known and/or desired density. Asphalt binders have been described to function as a water-resistant thermoplastic adhesive that "glues" the aggregates together. The asphalt binder is commonly a residue from petroleum refining chosen from certain crude oil blends processed to have suitable endurance and other functional properties. Additives (such as polymers) can be blended or reacted with the binder (to modify binder properties and enhance performance as is well known to those of skill in the art). See Anderson et al., *Asphalt Binders*, A2D01: Committee on Characteristics of Bituminous Materials, at URL, nas.edu/gulliver.trb/publications/millennium/00006.pdf.

Asphalt binders (as well as the selection of aggregates) can be customized for each site or project. The asphalt binders may be selected for a particular application, expected climate of operation/use, established maximum and minimum temperatures within a cycle, and/or other desired characteristics when designing a pavement mixture. Asphalt binders may be graded under the PG (performance graded) binder specification standard developed by the Strategic Highway Research Program (SHRP). In this grading system, the first two digits of the binder identifier can present an average 7-day maximum pavement design temperature and the last two digits can reflect an average 7-day minimum pavement design temperature. Thus, for example, a binder identified as PG 64-22 binder reflects an average 7-day maximum temperature of 64° C. and an average 7-day minimum of 22° C. The temperatures can be established using the SUPERPAVE (an acronym for "SUperior PERforming ashpalt PAVEments") weather database, which includes over 5,000 weather stations across the United States. The pavement temperatures can be calculated using air temperatures measured at the weather stations using well-known models.

Most paved roads in the United States are surface-paved with hot-mix formulations of asphalt containing generally about at least 93–96% aggregate and 4–7% asphalt binder (and typically including some number of air voids after compaction, such as between about 3–10%).

Stripping is a phenomenon of the loss of the bond between asphalt binder and the aggregate resulting in physical separation and degradation of the pavement. One of the common causes of stripping is the presence of water or moisture on and/or in the pavement. The potential for stripping due to moisture can be reduced by using anti-stripping additives in asphalt mixtures or asphalt binders. Examples of anti-stripping additives are hydrated lime, cement, polymer based and/or other liquid chemicals. Anti-stripping agents can be added in lesser amounts than either the aggregates or asphalt binder, such as between about 0.1–3%, and typically about 0.5–2% percent, of the total asphalt binder weight. For example, when hydrated lime is used, between about 1–2% of anti-stripping agents are used as compared to between about 0.5–1.0% for when other liquid chemicals are used, of the total asphalt binder weight.

In the past, the anti-stripping additives in the mixture could be indirectly evaluated through the performance of the asphalt pavement, such as by using standard test method AASHTO T283. Unfortunately, this method generally takes several days to obtain results. This delay and/or inconvenience may limit the number of inspections performed to verify the presence or level of anti-stripping agents in the asphalt mixtures. In addition, the potential variability in the dosage of anti-stripping additives employed, batch to batch, can introduce uncertainties in the quality of the paved roadway and may cause or contribute to premature degradation of the roadway surface.

In view of the above, there remains a need to provide economical methods and devices that can assess the presence and/or level of anti-stripping agents in asphalt related materials. There is also a need to provide anti-stripping agent tests that can be readily obtained and completed in reduced time so as to provide prompt reporting of the test results to facilitate increased numbers of inspection opportunities and/or increased control of the content of anti-stripping agents in asphalt binders or asphalt mixtures when delivered to construction sites.

SUMMARY OF THE INVENTION

The present invention is primarily directed to methods, systems, devices, and computer program products that can determine the presence of and/or the level of anti-stripping agents in asphalt materials such as in asphalt binders or asphalt mixtures.

In certain embodiments, the testing can be carried out relatively quickly. The devices may be implemented as portable units that can be used at field (construction paving) sites to evaluate a sample of hot-mix asphalt material to verify that an anti-stripping agent(s) is included and/or to evaluate that a sufficient amount of the agent has been added. Thus, the test may be carried out in situ just prior to a planned road mixture application and/or at a future date for forensic reasons.

In other embodiments, the anti-stripping agent may be combined with the binder material before the aggregate is added and the evaluation can be carried out on the asphalt binder and anti-stripping agent mixture at a laboratory, refinery, or mixture fabrication site.

In certain embodiments, the test can be carried out as a qualitative "go/no-go" or "pass-fail" test based on the confirmation that the anti-stripping agent is present and/or present in at least a threshold amount, in a sample of the asphalt binder or asphalt mixture. In other embodiments, the test may be carried out as a quantitative test to assess whether the amount or level of the anti-stripping agent in the asphalt binder or asphalt mixture meets the established design criteria.

The acidity or alkalinity of the asphalt sample can be analyzed. In certain embodiments, the asphalt sample can be in a flowable state and a liquid pH sensor can be employed to sense the pH of the sample. In other embodiments, the sample is held at a temperature sufficient to cause it to emit exhaust vapor that can be analyzed for pH or other volatile constituent(s), such as ammonia, or properties, that are measurable by suitable sensors.

The gas or vapor emissions may provide the anti-stripping agent in increased content relative to liquid form, potentially allowing for a more rapid and/or sensitive test. Thus, the gas or vapor emissions may be directly evaluated or monitored such as by placing a sensor in the vapor flow path. Alternatively, the gas or vapor may be indirectly monitored or evaluated. For example, the gas or vapor emissions can be directed to travel through a liquid media, such as de-ionized water, that is selected to allow the vapor or gas to induce or cause a detectable change of property in the liquid media (such as pH value). The change in property in the liquid media this is used to evaluate the vapor emission and, hence, the anti-stripping agent.

The pH sensor may be any suitable sensor type. In certain embodiments, the pH sensor is litmus paper and the color change of the litmus paper can be automatically analyzed and compared to a library of data of known concentrations of a corresponding anti-stripping agent to determine the level of anti-stripping agent in the sample.

Certain aspects are directed toward methods for analyzing anti-stripping agents in a sample comprising asphalt material. The method includes: (a) obtaining a sample comprising asphalt binder material; and (b) detecting at least one selected property and/or constituent associated with the sample to assess the presence or absence of at least one anti-stripping agent in the sample.

In particular embodiments, the method can include: (a) sensing the acidity and/or alkalinity of the sample; and (b) analyzing the sensed acidity and/or alkalinity to assess at least one of: (i) the presence of at least one anti-stripping agent in the sample; and (ii) the level of at least one anti-stripping agent in the sample.

In certain embodiments, the method can include capturing exhaust vapor emitted from the sample. As such, the analyzing step can include analyzing the captured exhaust vapor and the sensing step can be carried out by detecting a selected constituent and/or property of the vapor, such as the pH, ammonia, or the like, of the exhaust vapor.

In particular embodiments, the methods can include: (a) generating a reference library of pH (or other desired sensed data) corresponding to the detected alkalinity and/or acidity (or other desired parameter) of a plurality of known selected combinations of material binders and anti-stripping agents at a plurality of different concentrations; and (b) defining a plurality of mathematical calibration models, each corresponding to a predetermined combination of a selected material binder and anti-stripping agent which correspond to the presence and/or level of the anti-stripping agents in a sample undergoing analysis based on the generated reference library data.

The evaluation can be carried out by having a user identify the anti-stripping agent in the sample undergoing analysis and comparing data for the sample undergoing analysis to the mathematical model of the combination of the asphalt binder and the identified anti-stripping agent to determine the concentration, level and/or amount of anti-stripping agent present in the sample.

Other embodiments are directed to methods of analyzing anti-stripping agents in a sample comprising asphalt material. The methods include: (a) obtaining a sample comprising asphalt binder material; (b) capturing exhaust vapor emitted from the sample; (c) detecting the acidity and/or alkalinity of the captured exhaust vapor; and (e) determining, based on the detecting step, at least one of: (i) the presence of at least one anti-stripping agent in the sample; and (ii) the level of at least one anti-stripping agent present in the sample.

In certain embodiments, the method can include heating and/or pre-heating the sample to a sufficient temperature for a sufficient time to generate the exhaust vapor. The test can be carried out in a relatively rapid manner so that the detecting and determining steps are carried out in about 15 minutes or less, and, in some embodiments in about 10 minutes or less.

The method may include analyzing the exhaust vapor in an automated manner with at least one pH sensor to generate data representative of the pH of the exhaust gas. Further, the method can be carried out in an automated manner so that automated analysis is carried out using a spectrophotometer that measures color change in the reflectance spectrum of the wavelength of between about 400–700 nm in the visible range.

Still other embodiments are directed to systems for analyzing samples comprising asphalt binder materials for anti-stripping agents. The systems include: (a) a container having an enclosable chamber therein, the container configured and sized to hold a predetermined amount of sample comprising asphalt binder material in the enclosable chamber; (b) a sensor configured to be in fluid communication with the sample in the container chamber during operation; and (c) a predetermined quantity of sample comprising asphalt binder material combined with a liquid anti-stripping agent held in the enclosable chamber. In operation, the sensor detects the selected parameter (such as the alkalinity and/or acidity) of exhaust gas emitted from the sample when heated to a temperature sufficient to cause the transformation of a liquid anti-stripping agent to a gaseous vapor form.

The system may, in particular embodiments, also include: a primary housing sized and configured to provide an enclosed space; an optical detector positioned in the housing; a controller and operational circuitry in the housing that directs the timing and operation of the pH detection and automatically generates and provides the results of the evaluation; and a display having a user input device to allow communication interface between a user and the system.

In particular embodiments, the pH sensor comprises litmus paper, and the primary housing is configured to hold the container and to hold a heat source that is able to heat the sample in the container in a temperature controllable manner. The system can also include a pH sensor track and positioning guides that direct the pH sensor to follow a predefined travel path that extends between the enclosed chamber of the primary housing and the container to position the sensor in operable position in communication with the enclosed chamber of the housing and then retrieve the exposed pH sensor so as that, after a predetermined time, the pH sensor is moved to be in optical communication with the optical detector.

The optical sensor can be a spectrophotometer that is configured to detect color alterations in the reflectance spectrum. In certain embodiments, the system includes a computer program module that comprises computer program code that provides a plurality of different calibration models that define a mathematical relationship of pH and concentration of anti-stripping agent in a sample of predetermined size based on a priori analysis of representative combinations of asphalt binder materials and anti-stripping agents in differing concentrations in corresponding sample sizes.

Still other embodiments are directed toward computer program products for determining the level, amount, concentration and/or percent of anti-stripping agent present in a sample comprising asphalt binder material, of a sample undergoing analysis. The computer program product includes a computer readable storage medium having computer readable program code embodied in the medium. The computer-readable program code includes: (a) computer readable program code for accepting input identifying the type of anti-stripping agent in a sample undergoing analysis, the sample comprising asphalt binder material combined with anti-stripping agent in liquid form; (b) computer readable program code for obtaining sensor data for the sample undergoing analysis; (c) computer readable program code providing selectable calibration models based on predetermined mathematical relationships of the correlation of sensor data and the level of anti-stripping agent in a sample over a range of levels, amounts or concentrations of interest and exposure time with a different calibration model being provided for each of a plurality of different combinations of asphalt binder material types and different anti-stripping agents; and (d) computer readable program code for calculating the level, amount, concentration and/or percent of anti-stripping agent present in a sample undergoing based on the corresponding calibration model of the type of asphalt binder material and/or anti-stripping agent in the sample.

In certain embodiments, the computer program code that provides a plurality of different selectable calibration models is derived from an analysis of the relationship of representative pH and concentration values of anti-stripping agents in known samples of predetermined size based on a priori analysis of selected combinations of asphalt binder materials and anti-stripping agents in differing concentrations.

The pH data may be obtained and/or collected so as to comprises optical detectable variation in color in a pH sensitive substrate, and wherein the calibration model is derived from a range of reflectance values corresponding to differing values of color change in the reflectance spectrum of the pH sensitive substrate versus known greater and lesser amounts of anti-stripping agents present in different samples comprising asphalt binders.

In particular embodiments, the computer readable program code that calculates an index is based on the measured color change in the reflectance spectrum of the sample undergoing analysis and the product also includes computer program code that compares the calculated color index to the appropriate calibration model to determine the amount, level, or percent of anti-stripping agent in the sample. In other embodiments, the index is based on the measured intensity of a target color, or wavelength of the EM spectrum.

Other embodiments are directed to automated analysis systems for analyzing asphalt binder and/or asphalt mixtures for anti-stripping agent content. The systems include: (a) a container with a detachable lid defining an internal volume configured and sized to hold a predetermined amount of asphalt binder and/or asphalt mixture therein; (b) a primary housing defining an enclosed internal space and having a platform configured to hold said container; (c) a pH sensor having a substrate that alters in an optically detectable manner upon exposure to vapors emitted from a sample comprising asphalt binder and an anti-stripping agent disposed so that, during detection, the pH sensor being in fluid communication with the container internal volume; (d) a spectrophotometer disposed in the primary housing and configured to obtain measurement data of the optically detectable changes of the pH sensor; (e) a controller operatively associated with the spectrophotometer; and (f) a computer module operatively associated with the controller, the computer module comprising computer program code for determining the amount, level, and/or percentage of anti-stripping agent in the sample based on the measurement data provided by the spectrophotometer.

The automated system can be configured so that the spectrophotometer generates measurement data of color in the reflectance spectrum in the range of visible wavelengths. The computer module can include computer program code that provides a plurality of different selectable calibration models, the calibration models being derived from an a priori analysis of representative measured reflectance spectrum values versus known concentration values and exposure time of anti-stripping agents in known samples of predetermined size of selected combinations of asphalt binder materials and anti-stripping agents over a plurality of different concentrations.

Advantageously, the test methods and systems of the present invention are easy-to-use, and allow real-time on site testing protocols. The methods and systems can be used to analyze either asphalt binders (sans aggregates) or asphalt mixtures (with aggregates). Further, the systems, devices and methods of the present invention can reduce the amount of testing time required, typically down to a time on the order of between about 5–15 minutes.

Other embodiments are directed to kits of disposable pH sensor units that can be releaseably attached to an anti-stripping agent detection system. The kits include a plurality of single-use disposable pH sensor units. Each unit comprises a frame member having opposing first and second primary surfaces and opposing first and second end portions; and litmus paper attached to a first end portion of at least one primary surface of the frame member.

The foregoing and other objects and aspects of the present invention are explained in detail in the specification set forth below.

BRIEF DESCRIPTION OF THE DRAWINGS

FIG. 7A is a partial cutaway front view of the automated analysis system shown in FIG. 6 according to embodiments of the present invention.

FIG. 7B is an enlarged perspective view of an exemplary gas trap shown in FIG. 7A according to embodiments of the present invention.

DESCRIPTION OF EMBODIMENTS OF THE INVENTION

Figure 1:
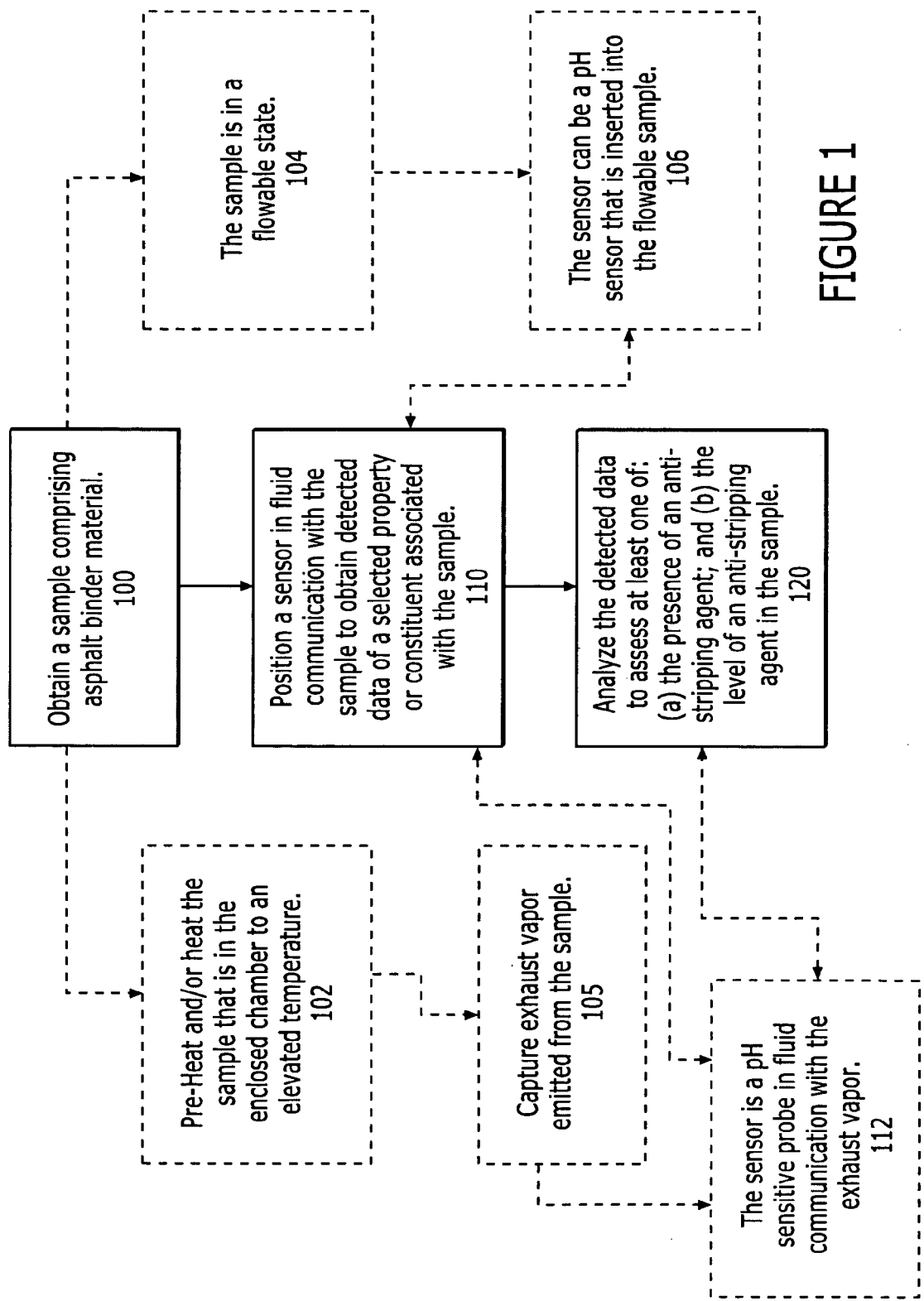
FIG. 1 is a block diagram of operations that can be used to assess asphalt materials for anti-stripping agents according to embodiments of the present invention.

The present invention will now be described more fully hereinafter with reference to the accompanying figures, in which preferred embodiments of the invention are shown. This invention may, however, be embodied in many different forms and should not be construed as limited to the embodiments set forth herein. Like numbers refer to like elements throughout. Layers may be exaggerated for clarity. In the block diagrams, broken lines indicate such operation or feature is optional.

Embodiments of the present invention are directed to evaluating asphalt materials. As such, samples comprising asphalt material such as asphalt binders alone or in combination with other additives can be evaluated, and/or asphalt mixtures with the asphalt binder combined with aggregate can be evaluated. In operation, a sample comprising the asphalt material of interest is obtained. The sample can be obtained and/or evaluated at a refinery, at a pavement mixing company fabrication site, at a field site, at a laboratory, or at a testing facility.

Typically, the asphalt mixture is produced based on a predetermined design that indicates the desired percentage of constituent components. The methods, systems, and computer program products provided by the instant invention can confirm that a sufficient amount of anti-stripping agent (s) is present and/or can quantitatively determine the level, amount, or percentage of anti-stripping agent in the asphalt material sample.

In particular embodiments, the asphalt material sample may be obtained and tested in situ at a field application site (as a quality inspection procedure) to evaluate the correct amount of anti-stripping agent is present before a particular batch is dispensed onto the roadway or paving structure.

The anti-stripping agent may be a single anti-stripping agent or plurality of different stripping agents that are added to asphalt binders. Examples of anti-stripping agents include, but are not limited to, hydrated lime (calcium oxide mixed with one or more of silica, alumina, and iron), cement, and other chemicals, typically in slurry or liquid (non-aqueous) form. Conventionally, the most commonly used anti-stripping agents are hydrated lime and liquid chemicals (alkaline-type) as is known to those of skill in the art. Anti-stripping agents can be added in lesser amounts than either the aggregates or asphalt binder, typically between about 0.1–3% percent of liquid chemicals as a percent of the total asphalt binder which may equate to about 0.025% of the total weight (asphalt binder plus aggregates).

The aggregate in the asphalt mixture may include both fine and coarse aggregates (and may also include dust or mineral filler), which can be separated and graduated according to well-known procedures, as needed for the material sample undergoing analysis. The aggregate material sample may also contain a plurality of different aggregate composition types.

When evaluating asphalt mixtures, the methods, systems and computer programs of the present invention can be used to evaluate asphalt mixtures comprising either or both fine and coarse aggregates. The term "coarse aggregate" is typically applied to mineral and/or synthetic aggregate material that is retained on a 2.36 mm (No. 8) sieve. The term "fine aggregate" applies to material passing through the 2.36 mm (No. 8) sieve. Mineral filler or fine aggregate (including "very fine" aggregate) is applied to material of which at least 70% passes through a 75 μm (No. 200) sieve. Asphalt pavement and/or asphalt concrete specifications typically require that the aggregate particles are within a certain range of sizes and that each size is present in a certain proportion. The aggregate mixture may include aggregates of different shapes as well as aggregates of different material types. For example, many asphalt mixtures contain both angular and rounded aggregate particles. The coarse aggregate particles can be a crushed stone or gravel and the fine aggregate can be a natural sand (round particles) or stone screenings. The term "porous or absorptive materials" includes materials that have a tendency to have voids, such as asphalt coated aggregate particles, and/or materials which have greater than or equal to about 2% by weight absorption.

The sample can be selected such that it is sized on the order of between about 50–5000 g. For example, for asphalt material samples that have not been combined with aggregates, a smaller sample size may be used, typically between about 50–500 grams, and more typically between about 100–300 grams. For asphalt mixtures (with aggregates), the sample size can be increased to between about 1000–5000 grams, more typically between about 2000–4000 grams.

Turning now to FIG. 1, operations suitable for evaluating asphalt material samples are illustrated. As shown, a sample comprising asphalt binder material is obtained (block 100), and a sensor is positioned in fluid communication with the sample (block 110) to obtain sensed sample data of a selected parameter (property or constituent associated with the sample). The sensed data is analyzed to assess at least one of: (a) the presence of an anti-stripping agent in the sample; and (b) the level of an anti-stripping agent in the sample (block 120).

For ease of discussion, the sensor will be described as a pH sensor used to assess alkalinity or acidity of the sample or its exhaust vapor, but other sensors can be used and/or other properties or constituents of the sample can be sensed, evaluated and/or interrogated.

In certain embodiments, the sample can be treated, i.e., typically warmed or heated so that it is in a flowable state during the evaluation (block 104) and the pH sensor can be inserted directly into the flowable sample (block 106) to obtain the sample pH data. The flowable state allows the anti-stripping agent to be in a liquid or flowable state. Alternatively, the sample can be heated or pre-heated to a temperature sufficient to cause it to emit an exhaust vapor. In certain embodiments, the sample may be preheated and/or heated and positioned inside an enclosed chamber (block 102). The exhaust vapor emitted from the sample can be captured (block 105) and the pH sensitive probe or sensor can be positioned so as to be in fluid communication with the exhaust vapor to obtain the sample pH data (block 112). For the liquid analysis larger samples and/or increased testing time may be needed relative to the vapor based evaluations. Thus, in the vapor-based detection embodiment, the pH sensor is configured to detect alkalinity and/or acidity (pH) in vapor emitted from the sample, rather than from inside the physical sample itself. The emitted exhaust vapor will have an increased amount of anti-stripping agent in it compared to the physical sample (where it is a minor constituent in the binder or mixture).

The pH sensor can be any suitable sensor, including a liquid sensor or a gas sensor, that is sufficiently sensitive to detect the amount of anti-stripping agent in the asphalt sample (which can be somewhat diluted relative to the contents of the sample itself). Examples of pH sensors that may be suitable include, but are not limited to, gas chromatograph devices, autonomous chemical sensors (such as the pH/ORP sensors or SAMI-pH sensor available from Sunburst Sensors, LLC.), pH sensors that employ fluorescence-based detection activity (such as optrode optical sensors from Ocean Optics, Inc. and/or those described in Lin et al., *Lifetime-Based pH sensors: Indicators for Acidic Environments*, Analy. Biochem 269, 162–167 (1999), electronic circuitry-based sensors (such as ISFET pH sensors, electrode-based sensors, micro pH sensors, or electrodeless sensors, see e.g., Broadley James at broadly james.com, ABB Automation, LTH Electronics Inc.), Greenspan and/or Stevens-Greenspan pH sensors (enviro-analytical.com and/or stevenswater.com), an electronic nose-style sensors, electrochemically synthesized polymer-based pH sensors (stii.dost.gov), and pH sensors with pH-sensitive substrates that undergo an optically detectable change when exposed to alkalinity and/or acidity (such as litmus paper and the like).

As noted above, in other embodiments, another selected property or (volatile) constituent of the gas or vapor emission can be monitored or detected and sensors selected accordingly. For example, the amount and/or presence or absence of ammonia can be monitored. Additionally, the sensor may be placed directly into the flow path of the gas or vapor emission to directly detect the selected property and/or constituent. In other embodiments, the sensor may be selected and positioned in communication with the vapor emission to analyze the vapor or emissions indirectly. For example, the vapor emission can be directed to percolate or flow through a selected medium (such as de-ionized water) causing the selected medium to undergo a change in a selected property or to produce a constituent or a constituent of an induced chemical reaction caused by the vapor emission, the property and/or constituent in the medium being sensed to evaluate the anti-stripping agent, as discussed above.

Figure 2:
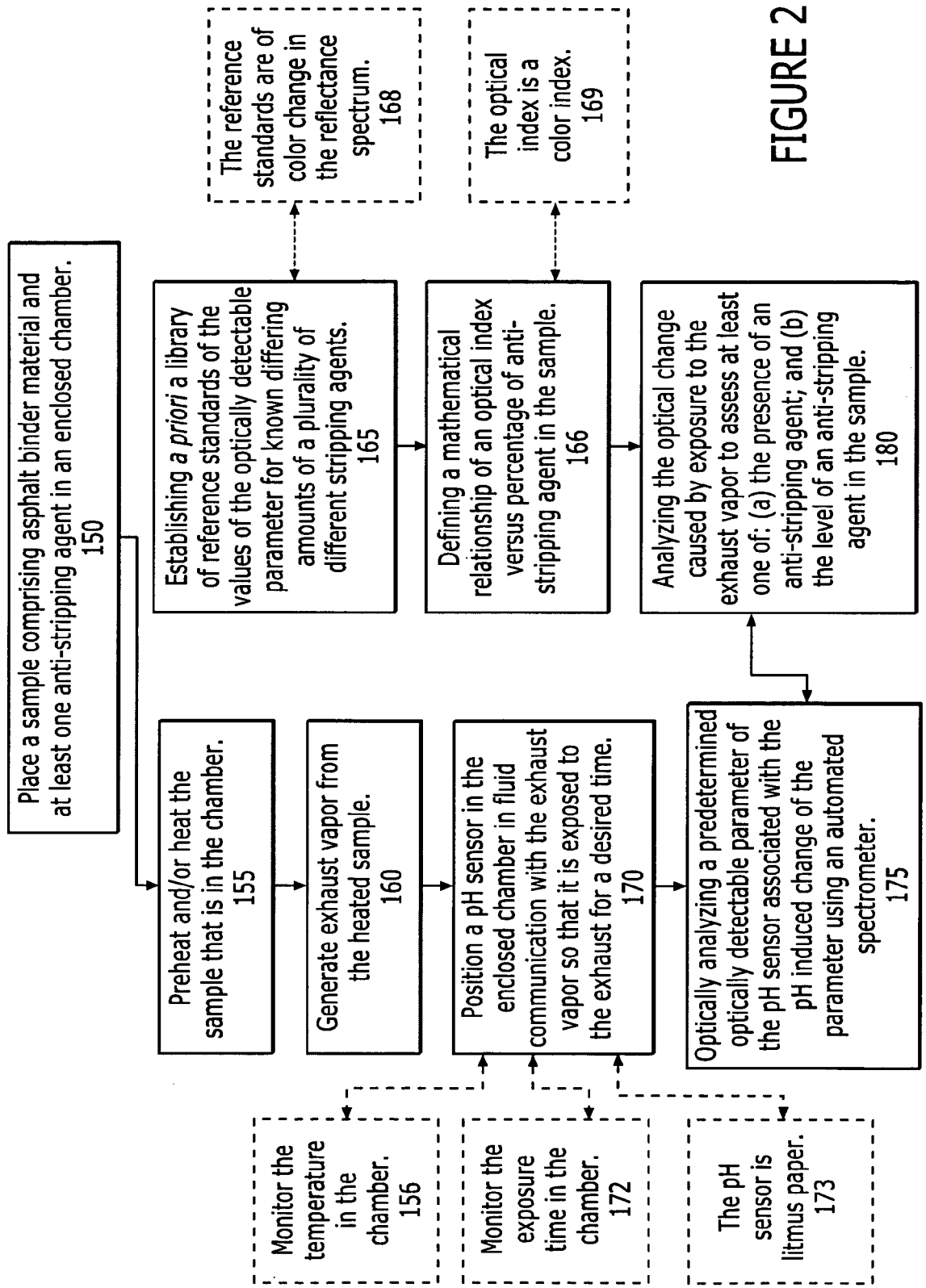
FIG. 2 is a block diagram of operations that can be used to assess anti-stripping agents in asphalt materials according to other embodiments of the present invention.

FIG. 2 illustrates operations that can be used to evaluate a sample comprising asphalt binder material and at least one anti-stripping agent in an enclosed chamber (block 150). Exhaust vapor can be emitted from a heated sample (block 155). The sample can be heated in the chamber and/or preheated before it is placed in the chamber (block 160). In certain embodiments, the sample can be obtained from a "hot-mix" asphalt mixture so that the sample at the time of selection already has been elevated to a sufficient temperature to cause it to emit exhaust fumes or vapors.

In embodiments that use the vapor to evaluate the anti-stripping content of the sample, because some ingredients of liquid anti-stripping chemicals have strong volatile properties under heat, the heating process creates a phase change of ingredients from liquid to vapor, separating the additive from the sample. The vapor, which contains some ingredients of the anti-stripping agent (chemical or constituents thereof) is then measured using a suitable pH detector or sensor to detect the presence and/or level of the anti-stripping agent.

In certain embodiments, as shown in FIG. 2, a pH sensitive probe that changes in an optically detectable manner or characteristic can be used as the pH sensor and positioned in the enclosed chamber in fluid communication with the exhaust vapor so that it is exposed to the exhaust for a desired amount of time (block 170). The optically detectable parameter may be one or more of: intensity, opacity, translucence, transmittance, reflectance, color, fluorescence, and the like. The optically detectable parameter may be visually detectable by eyesight. In certain embodiments, the alteration in the optically detectable parameter is detectable by an automated machine or optical detector such as a spectrometer (e.g., spectrophotometer) and the like (block 175).

In particular embodiments, the pH sensor can be litmus paper that changes in color when exposed to alkalinity or acidity (block 173). The optically detectable characteristic used to evaluate litmus paper can be reflectance associated with the color change of the exposed litmus paper that can be optically analyzed using an automated photo-spectrometer (block 168). In the embodiments employing litmus paper as the pH sensor, due to the relatively minor amount of liquid anti-stripping agent (by volume) in the sample, the color change can be less than about 3 color graduations (on a 12 gradient scale), and more typically, about two graduations or less will be caused upon exposure to the emitted vapor during the evaluation.

During the evaluation, the time and/or temperature of the sample in the chamber (blocks 156, 172) may be monitored during the exposure period.

A library of reference standards for known ("controlled") differing amounts (levels, concentrations, exposure times and the like) of a plurality of different stripping agents and associated optical change in the sensor (such as a pH sensor) type employed can be established a priori (block 165). In certain embodiments, the library of known values can be established using color reflectance values in the reflectance spectrum in the visible wavelength range, such as between about 400–700 nm (block 168). Other embodiments analyze other parameters such as, but not limited to, intensity of a specific color or wavelength in the EM spectrum.

A mathematical relationship can be defined that provides a calibration curve or look-up chart (or equation) that correlates detected concentration in the unknown sample to the detected change, allowing a computer to automatically determine the concentration upon input of the optically detected value (block 166). The mathematical relationship may be a curve, equation or look-up chart that is established by extrapolating and/or interpolating the relationship of at least three different concentrations and associated optical values of the parameter of interest of the known samples.

In certain embodiments, the mathematical relationship can be established using a number or a "index" that can be defined. The index gives a numerical identifier associated with the detected parameter across potential color variations for various concentrations or percentages of anti-stripping agent in a sample across the pH range of interest (block 169). In particular embodiments, the index is a "color" index and the mathematical relationship may be a curve that is established by correlating, extrapolating and/or interpolating the relationship of at least three different concentrations and associated colors of the known samples.

The optically detectable change caused by exposure to the exhaust vapor can be analyzed to assess at least one of: (a) the presence of an anti-stripping agent; and (b) the level (amount, percentage, or concentration) of an anti-stripping agent(s) in the sample undergoing analysis (block 180).

Thus, according to certain embodiments, the liquid anti-stripping agent in the asphalt material sample (whether asphalt binder or asphalt mixture) can be separated from the asphalt material through a volatilization process. To cause the sample to emit the anti-stripping agent in vapor form, the asphalt sample can be heated and/or preheated to a desired temperature. In particular embodiments, the sample can be placed in an oven or other heating device until the temperature of the sample reaches a desired targeted temperature. For example, the sample can be heated to at least about 280° F. (on average as measured internally). Other temperature settings can be used (and may be established by the user or an OEM or testing facility) depending on the type of asphalt binder and the type of anti-stripping agent undergoing evaluation.

The sample can also be exposed to increased pressure as well as heat to facilitate the release of vapor emissions. Pre-heating the sample can reduce the amount of time needed to run the test in the container or system. In certain embodiments, the heating of an ambient temperature or "cold" sample can be carried out so as to pre-heat the sample or hot plate to between about 80–300° F. (which may take a time period of a few hours). During the evaluation, the sample should be maintained at a temperature of above a predetermined threshold measurement temperature for at least 5 minutes. Preferably, the sample is evaluated as the temperature approaches the designated threshold temperature versus waiting for excessive time after the sample reaches the threshold temperature to begin the evaluation (doing so may disadvantageously allow an excess release of exhaust gases or vapors prior to the evaluation).

Figure 3A:
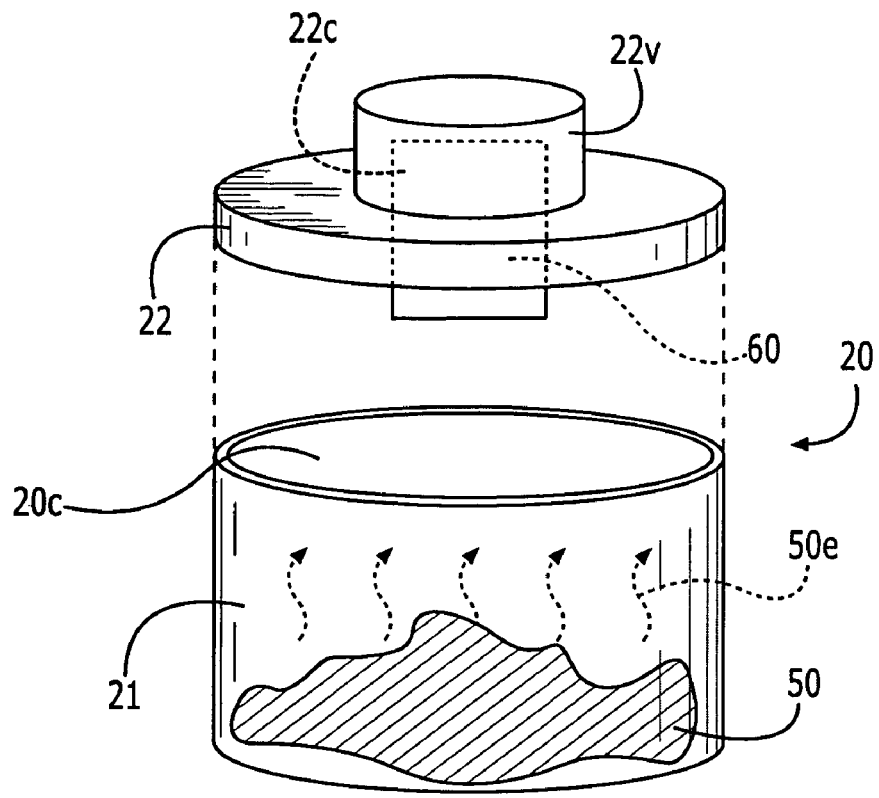
FIGS. 3A–3D are schematic illustrations of an evaluation container and a series of operations that can be carried out to analyze an asphalt material for an anti-stripping agent(s) according to embodiments of the present invention.
Figure 3B:
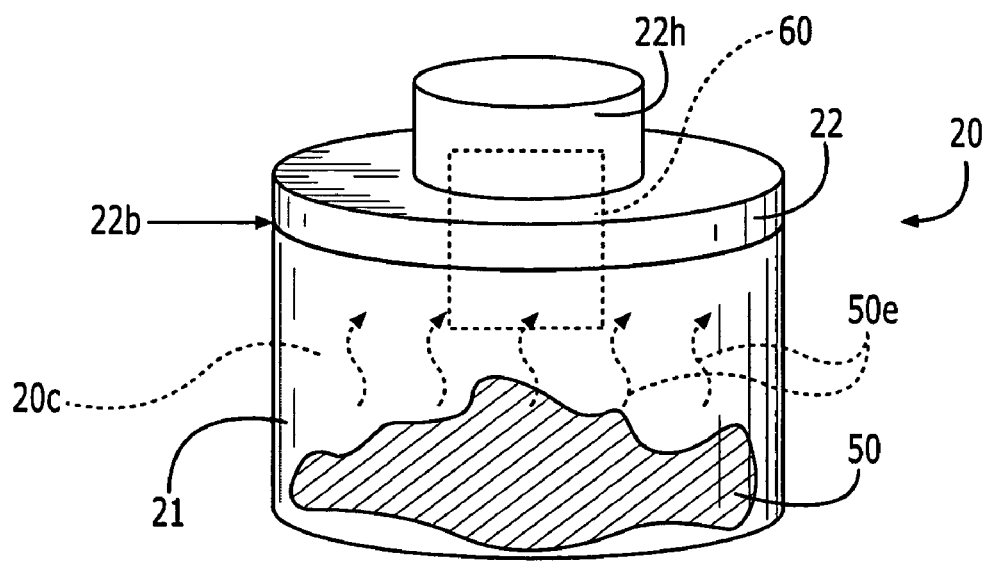

FIGS. 3A–3B illustrate one example of a collection or evaluation container 20 with an evaluation chamber 20c that may be employed according to certain embodiments of the present invention. The evaluation container 20 may include a bottom body portion 21 that is configured to provide the primary portion of the evaluation chamber 20c and a detachable lid 22, to allow the sample 50 to be positioned in the chamber 20c and then to substantially enclose the chamber 20c to provide a vapor capture region. A pH sensor 60 can be positioned in the container 20 so that it is in fluid communication with the exhaust vapor 50e during evaluation. As shown, the pH sensor 60 may be positioned on the underside of the lid 22l (FIG. 3C), so that the exhaust vapor 50e can flow upwardly and approach it from multiple directions during evaluation.

Figure 3C:
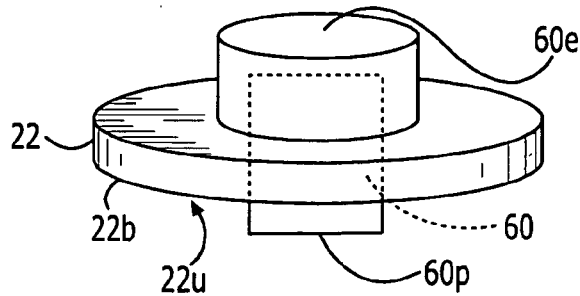

In certain embodiments, as shown in FIGS. 3B and 3C, the pH sensor 60 can be configured to extend downwardly from the underside of the lid 22u to extend a distance beyond the perimeter of the lower primary surface 22l of the lid. The extension can be sufficient to position the lowermost portion of the sensor 60p below the lower boundary 20b of the lid in the chamber 20c as shown in FIG. 3C. Operational electronics, where used (indicated by reference number 60e) may be sealed off from the active portion (or nose) of the probe 60p of the pH sensor 60, such as in a housing recess portion 22h formed in the lid, so that potentially sensitive electronics are protected and not in fluid communication with the vapor, for environmental protection. The container 20 can be configured as an integrated compact evaluation unit that does not require external support. In other embodiments, the container 20 can be configured to engage an evaluation system that can accept data from the sensor 60.

The container 20 may configured to provide a totally closed or sealed chamber 20c or configured to provide release of the vapor 50e that is emitted or exhausted from the heated and/or preheated sample 50. Thus, the container 20 may be configured with one or more orifices, apertures or other release means (not shown) to provide positive airflow to direct the captured gas 50e in the chamber 20c to flow by the pH sensor 60. In other embodiments, the container 20 can be closed by matably attaching the lid 22 to the container body 21 and allowing the heated vapor to rise in a natural manner for a desired time. The closure may be a sealed air-tight closure or a sufficiently snug closure to inhibit premature release of the captured gas 50e. In still other embodiments, active forced air systems and related devices such as air suction members, pressure relief valves, vacuums, fans, pressure chambers and the like can be used to provide the positive airflow in the chamber 20c (not shown).

In certain embodiments, the lid 22 can be configured with an extension component 22c that can be configured to hold the sensor 60 and be separately released from and attached to the lid 22. The extension component 22c can act as a grasping handle and may be formed of a thermally resistant material. The extension component 22e may be translucent, transparent or otherwise configured to allow viewing access to the pH sensor 60 and/or the internal chamber 20c during operation.

Figure 3D:
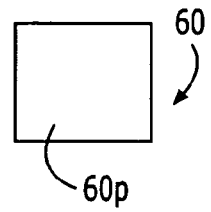

As shown in FIG. 3D, the pH sensor 60 may be a pH paper that is color-sensitive to alkalinity or pH, such as pH litmus paper. As such, in this embodiment, the nose of the pH sensor is the litmus paper 60p that can be held suspended from the extension component 22e, or attached to the lid or upper portion of the body of the container 21 (above the sample) in a manner that allows sufficient exposure to the vapor 50e during evaluation. The lid 22 and/or extension component 22e may be configured with a litmus support clamp or other detachable means (not shown) to hold the litmus paper 60p and allow easy replacement for the next test. To analyze the test results, the litmus paper 60p may be visually reviewed by a user to assess anti-stripping content (such as by comparing to a standardized guide provided for easy comparison and/or conversions of content or "pass/fail" test results). In other embodiments, the exposed litmus paper 60p can be reviewed by an automated image or optical processor (such as a photometer or other optical detector, as will be discussed further below).

Figure 4:
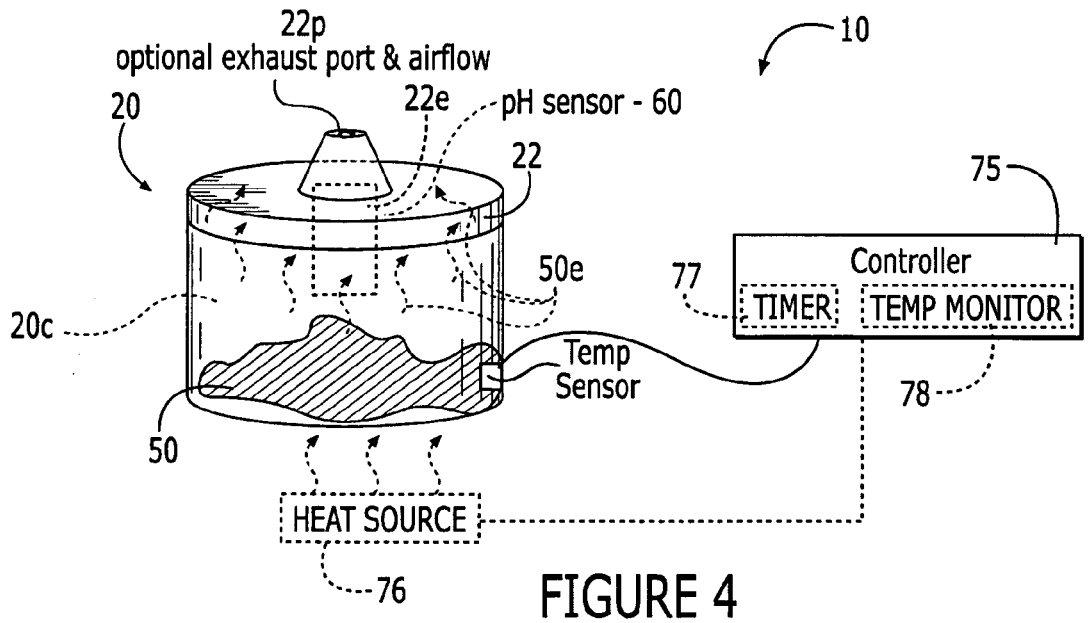
FIG. 4 is a schematic illustration of an analysis system according to certain embodiments of the present invention.

FIG. 4 illustrates one automated or semi-automated system with the container 20 operatively connected to a controller 75 that directs the timing or duration of the test. That is, once the lid 22 is closed, the test acquisition of pH data can be initiated. Once engaged, and/or at initiation of the testing protocol, the lid 22 may be locked in position until a predetermined exposure time has accrued. As such, the controller 75 can be in communication with a timer 77 and, in certain embodiments, a temperature monitor 78 that provides temperature data from a temperature sensor in communication with the chamber 20c (and/or sample 50) to ensure that the sample has a sufficient elevated temperature during the active sensing period. In certain embodiments, a heat source 76 may be positioned to provide heat to the sample in the container before and/or during the active sensing period. The controller 75 can also be configured to direct the application and/or temperature of the heat generated by the heat source 76. FIG. 4 also illustrates that an optional exhaust port 22p may be positioned in the extension component 22e above the sensor 60.

Typically, the evaluation time in the chamber 20c is predetermined based on the sample 50 type and/or size. To initiate the active sensing evaluation, a predetermined amount (volume or weight) of a sample 50 of material comprising asphalt (asphalt material) is placed in the container 20. The evaluation period and associated timing can start when the sample is at a desired threshold temperature (or for preheated only applications) upon placement into the container 20. The container 20 may be configured with thermally insulating materials. Where heat is applied during the evaluation, the container 20 can also include thermally transmissive portions to allow for efficient transfer of energy thereto.

In certain embodiments, the container 20 is closed and the emission or exhaust vapor 50e allowed to travel in a direction to expose the pH sensor 60 for about 30 minutes or less to obtain the desired data regarding the anti-stripping agent content in the sample. In certain embodiments, once the sample 50 is heated to a predetermined temperature threshold, the test can be carried out by actively sensing the sample emissions in the container 20 for about 15 minutes or less, and typically about 10 or less minutes, and, in particular embodiments, may be about 5 minutes or less. In any event, the sample of asphalt can be placed into an encloseable sample evaluation chamber for measurement. In operation, the exhaust vapor 50e flows through the designed air path to an enclosed measurement chamber 20c. Since sample weight, sample temperature, volume of vapor, and the time of exposure are precisely fixed for each sample, the sensed pH (or other property or selected constituent) can be attributed to the level of anti-stripping chemicals in the vapor.

Figure 5A:
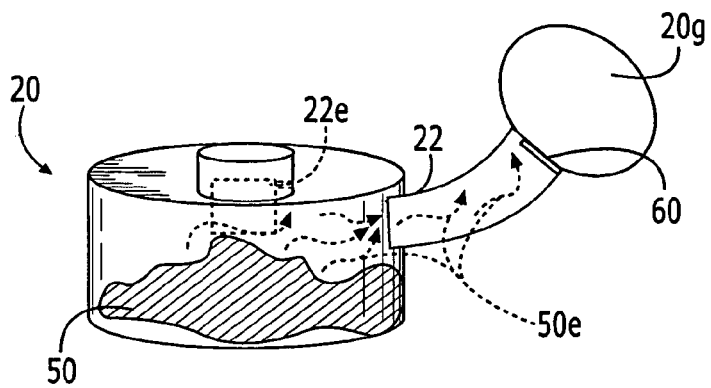
FIGS. 5A–5C are front perspective views of exemplary direct evaluation system containers according to embodiments of the present invention.
Figure 5B:
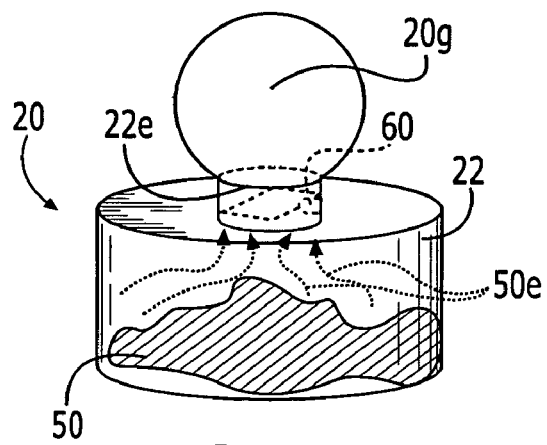
Figure 5C:
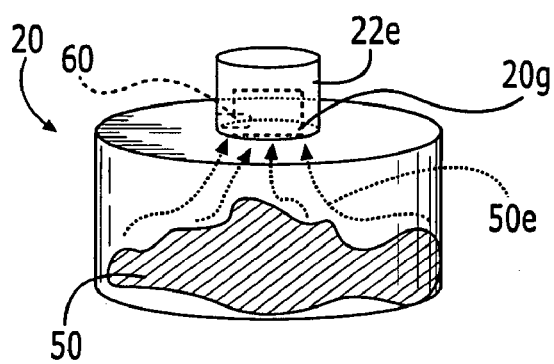

Referring to FIGS. 5A–5C, in certain embodiments, the evaluation container 20 can include a gas trap 20g that is in fluid communication with the primary chamber 20c. The gas trap 20g can be configured with a reduced size and volume relative to the primary chamber 20c. For example, as shown in FIGS. 5B and 5C, the extension component 22e may be configured to provide the gas trap 20g into which a sufficient amount of the exhaust 50e travels. The pH sensor 60 can be positioned in the gas trap 20g. As shown in FIG. 5B, the sensor 60 may be held across a width of the channel of the gas trap. Alternatively, as shown in FIG. 5C, the sensor 60 may be vertically oriented in the gas trap 20g. Other orientations may also be employed as long as the sensor is allowed sufficient exposure to the emissions 50e. In any event, the pH sensor 60 may be disposed to reside in the extension component 22e itself rather than the primary chamber 20c. In other embodiments, the gas trap 20g is a separate component as shown in FIG. 5A. The gas trap 20g may be formed into the side of the container body 21 rather than the lid 22. As before, the pH sensor 60 may be oriented in a substantially horizontal orientation across a portion (or all) of the width of the channel forming the gas trap 20g or the pH sensor 60 may be configured to extend in a substantially vertical orientation in the extension 22e. Again, angular orientations of the sensor 60 in the gas trap 20g may also be employed. The gas trap 20g may be configured as a bulb (FIGS. 5A, 5B) or cylindrical (FIG. 5C) shape. Other gas trap configurations can also be used, such as boxes, as may more complex shapes to provide the desired volume of exhaust gas suitable to provide a sufficient amount of exposure to the anti-strip fumes in the testing time desired.

The volume of the vapor inside the measurement chamber (20c and/or 20g) and the sample temperature can be monitored and controlled by the controller 75 (i.e., which can include a microprocessor or computer). The time of exposure can also be accurately set for each type of sample undergoing evaluation. Where litmus paper is used as the pH sensor, the anti-stripping chemical in the vapor reacts with the litmus paper, and creates a noticeable color change. In certain embodiments, after exposure, the litmus paper can be transferred to a spectrophotometer to measure the color change. The spectrophotometer can be configured to measure a desired optical characteristic. For example, transmission, absorption, reflectance, and the like. As described above, in certain embodiments, the spectrophotometer can measure the reflectance spectrum of the litmus paper in the wavelength of the whole visible range.

Generally described, in certain embodiments, the pH sensor 60 can be a disposable single-use sensor. In other embodiments, the pH sensor 60 can be a multi-use sensor that can be used across multiple evaluations of different samples. In addition, in certain embodiments, the evaluation systems 10 can include a moving track that can be used to automatically select, position, and retract the sensor (or individually select and position a plurality of pre-loaded sensors) from a resting position, to its operative proximity to the container 20, then to a reader such as an optical detector or other suitable pH data collection device.

Figure 5D:
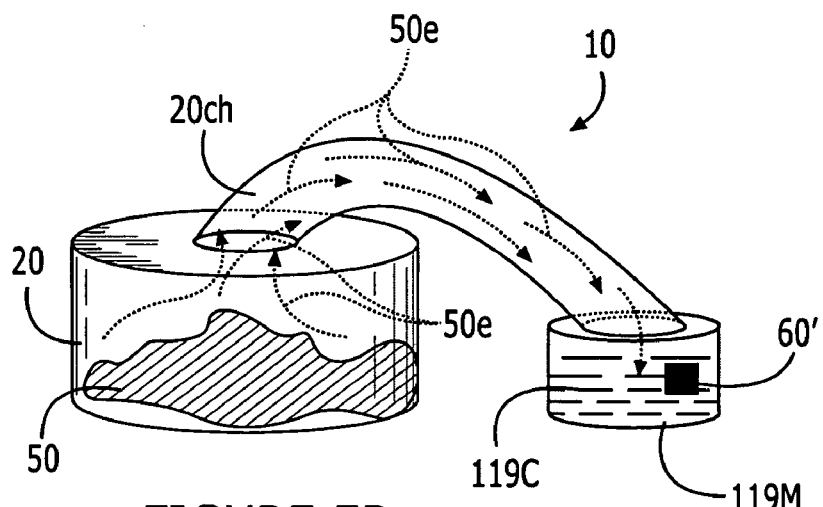
FIG. 5D is a front perspective view of an exemplary indirect evaluation system according to embodiments of the present invention.

FIG. 5D illustrates an example of an indirect sensing system 10'. As shown, the vapor emission 50e can be directed to percolate or flow from the sample container 20 to a flow channel 20ch and to or through a selected medium 119M held in a subcontainer 119C, shown as a liquid medium (such as de-ionized water), causing the selected medium 119M to undergo a detectable change in a selected property and/or to produce or increase a constituent in the medium 119M. The medium may be provided so that it generates a property or constituent that is induced by chemical reaction with the vapor emission 50e. A sensor 60' operably associated with the medium 119M is used to detect a selected property and/or constituent in the medium 119M induced or,caused by the exhaust directed therein to evaluate the anti-stripping agent, as discussed above.

Figure 6:
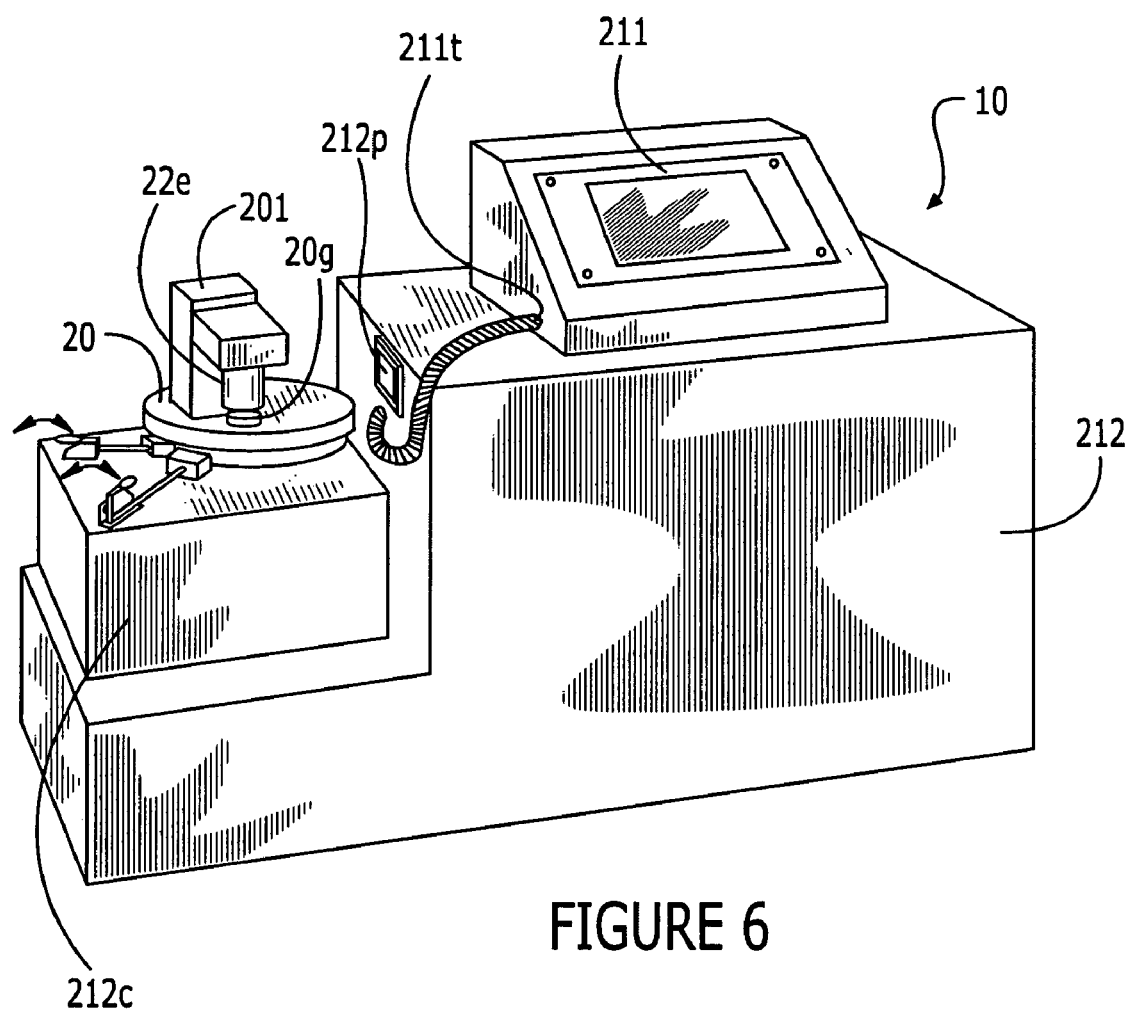
FIG. 6 is a front perspective view of an automated analysis system according to embodiments of the present invention.

Turning now to FIG. 6, one example of an automated analysis system 10 is shown. The system 10 includes a primary housing 212 configured to hold electronic (i.e., controller, power supply, and the like) and mechanical drive devices. As shown, the system 10 also includes a display 211 with a user interface (shown as a touch screen input), the container 20, a receiving chamber 212c sized and configured to receive and hold the container 20, and an arm 201 that overlays the container 20 helps hold the assembly in position. As shown, the container 20 includes a lid 22 with an extension component 22e. In this embodiment, the extension component member 22e is a separate component from the lid 22 that is sized to overlie a port 22p formed in the lid 22 with its lower end portion residing against the upper surface of the lid 22. Other attachment configurations may also be used.

Figure 8:
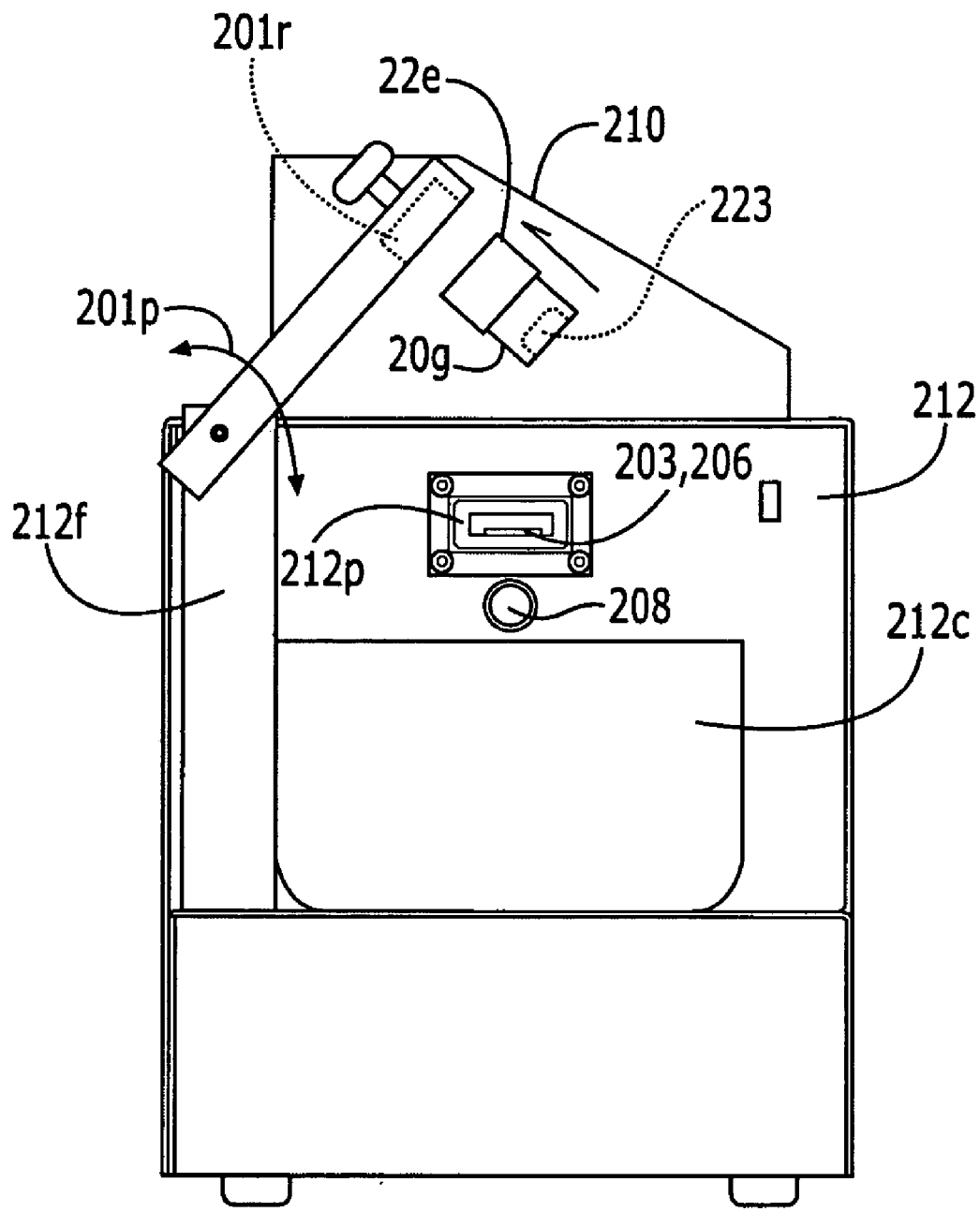
FIG. 8 is an end view of the system shown in FIG. 7A.

The arm 201 can be configured to rest against the upper end portion of the extension to hold the extension component against the lid 22. Referring to FIG. 8, the arm 201 can include a pivot attachment 201p to the frame of the housing 212f to allow the container to be positioned in the receiving chamber 212c of the housing and may include a recess 201r is configured to receive and frictionally engage the upper end portion of the extension member 22e when in proper position. The extension component 22e defines the gas trap evaluation chamber 20g. The extension component 22e can be configured as a single use disposable item. The extension member 22e may be transparent or translucent as shown in FIG. 6. In operation, the emission or exhaust vapor from the heated sample rises or percolates to enter the gas trap chamber 20g.

FIG. 7A illustrates that the arm 201 may also include a spring-loaded member 201s that can help force the extension component 22e against the lid 22. FIG. 7A also illustrates that, in this embodiment, the system 10 includes a disposable pH sensor 60 comprising pH paper 206 held by and/or mounted to a frame member 203. The pH paper 206 is attached to the underside of the frame member 203 (such as via double sided adhesive tape or other attachment means). The gas trap 20g includes a relatively narrow sensor port 223 that is sized and configured to allow the sensor 206 and frame member 203 to enter the channel (sized to allow entry and release of the sensor 203 and frame member 206, while not being oversized so as to inhibit the amount of exhaust gas that might leak from this port 223). The sensor port 223 may be formed in the gas trap 20g so that it defines a horizontally planar access window as shown, or other desired configuration, such as but not limited to, a vertically planar access window (not shown). The pH paper 206 may be about 0.5 inches×1 inch long and sized so that, in position, it spans a major portion of the width of the gas trap channel as shown in FIG. 7A. FIGS. 7B and 8 illustrate that the frame member 203 can be substantially planar and oriented to reside in a horizontal orientation as it enters and resides in the gas trap 20g. The extension component 22e may have an open or closed upper end. FIG. 7B illustrates a closed end configuration. In the open-end embodiment, the arm 201 may overlie and enclose the chamber of the gas trap 20g to provide the closure to inhibit premature release of the exhaust gas. Similarly, the arm 201 may include apertures or release means to facilitate positive airflow where desired.

The opposing end portion of the frame member 203 can be held by a clamp or grasping mechanism 209 (FIGS. 7A, 7B) that holds the frame member 203 and is connected to an automated positioning system 215 or track guide system having a predetermined travel path. In operation, in response from the controller 75 (FIG. 4) the positioning system can automatically translate the frame member 206 with sensor 203 from a resting position in the housing 212 out of a housing port 212p (FIG. 8) into the chamber 20g, then retract the exposed sensor 206 mounted to the frame member 203 back into the housing 212 as shown in FIG. 12C. In the embodiment shown in FIGS. 7A and 12C, the automated positioning system 215 is a linear slide 213 connected to a stepper motor (not shown). Chain drives, conveyors, belts, gears, cams, mechanical linkages, and the like can also be used to provide the desired automated translation and positioning.

As shown in FIG. 7A, the system 10 can also include a photocell 208 or infrared sensor that is configured to indicate when the container 20 is in position in the housing chamber 212c. As is also shown, the system 10 can also include a spectrophotometer 207 held in the housing 212 and positioned in cooperating relationship and alignment with the moving track system of the frame member 203 and sensor 206, so as to be able to be in optical communication with the sensor 206 (prior to and/or after exposure).

Figure 9:
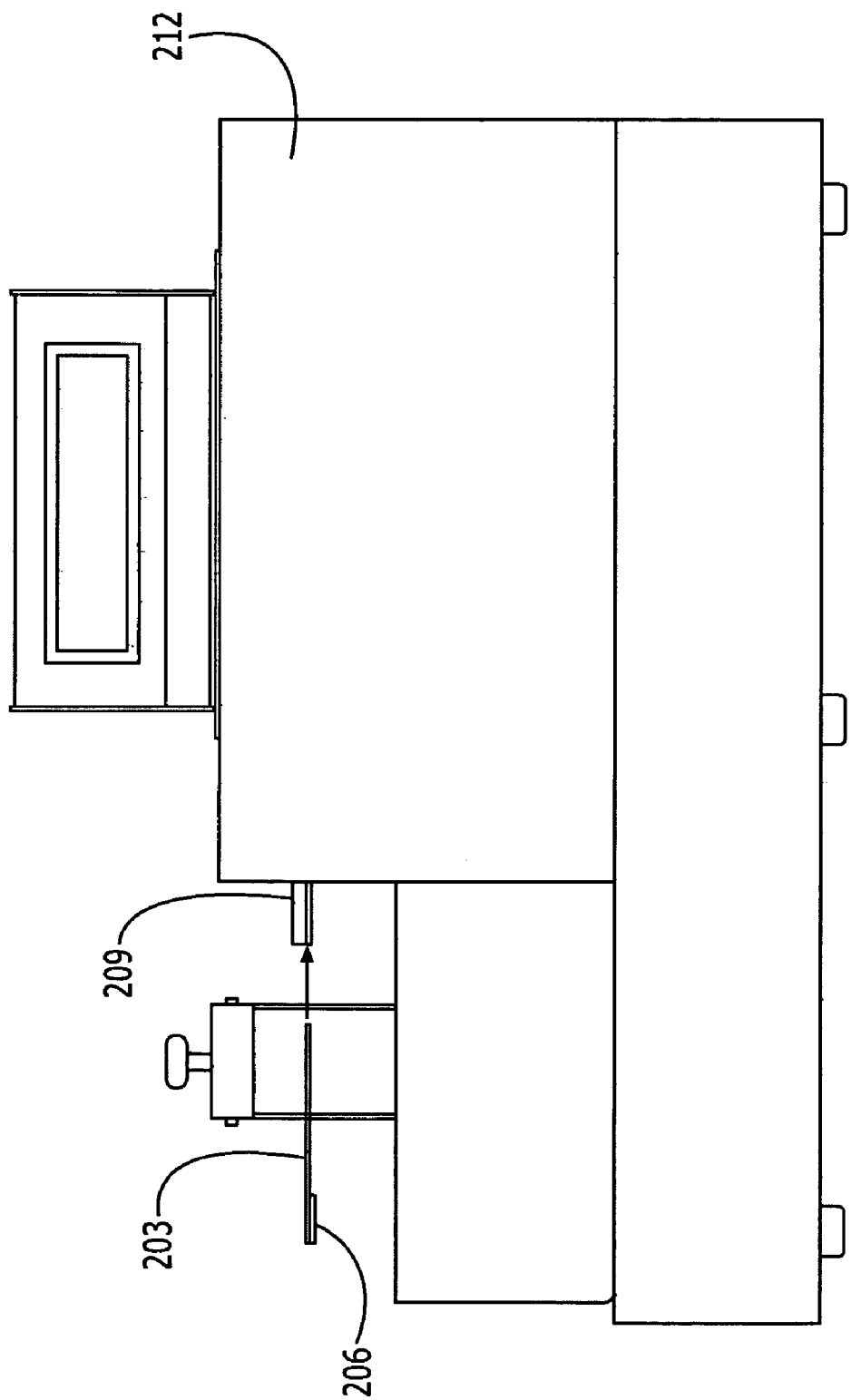
FIG. 9 is a front view of the system shown in FIG. 7A illustrating an exemplary loading of an automated positionable pH sensor according to embodiments of the present invention.

FIG. 9 illustrates that the pH sensor 206 and associated frame member 203 can be preloaded into the housing 212 and connected to the automated positioning system 215. The sensor paper 206 can be pre-attached to the frame member 203 at an OEM facility or at the test site by the user. In addition, a plurality of such assembled sensors can be held on reserve in the housing and the automated system configured to automatically select and serially advance individual sensors from a non-use (storage) position for a plurality of different evaluations. The housing 212 may include a cooling fan to cool the electronics and/or provide positive airflow out of the housing so as to inhibit contaminants or exhaust gas from entering the housing 212. Similarly, the port 212p can include a door or sealant means (not shown) to protect the internal contents of the housing 212.

Figure 10:
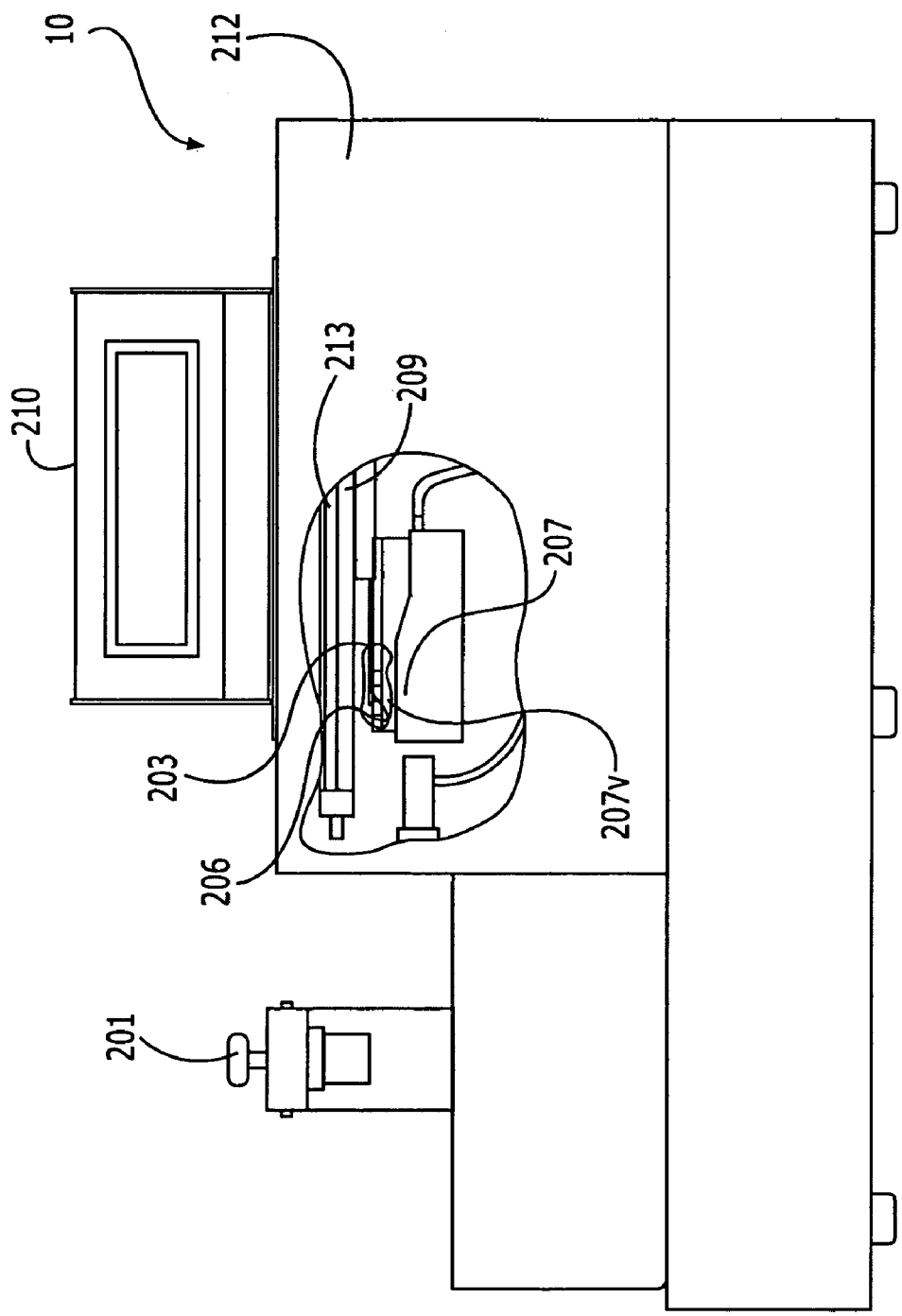
FIG. 10 is a partial cutaway front view of the system shown in FIG. 7A, but with the evaluation container and sample removed from the system according to embodiments of the present invention.

In certain embodiments, as shown in FIG. 10, after loading the sensor and frame member 203, 206, and/or just prior to insertion into the gas trap 20g, the sensor 206 can be positioned in the housing 212 in optical communication with the spectrometer 207. As shown, the optic viewing region 207v is positioned under the downwardly facing sensor paper 206 in parallel to the linear slide drive 213. Of course the optic viewing region 207v can be positioned in alternative locations and orientations and the automated positioning or drive system configured to guide the sensor 206 into the desired detecting alignment position.

Figure 11:
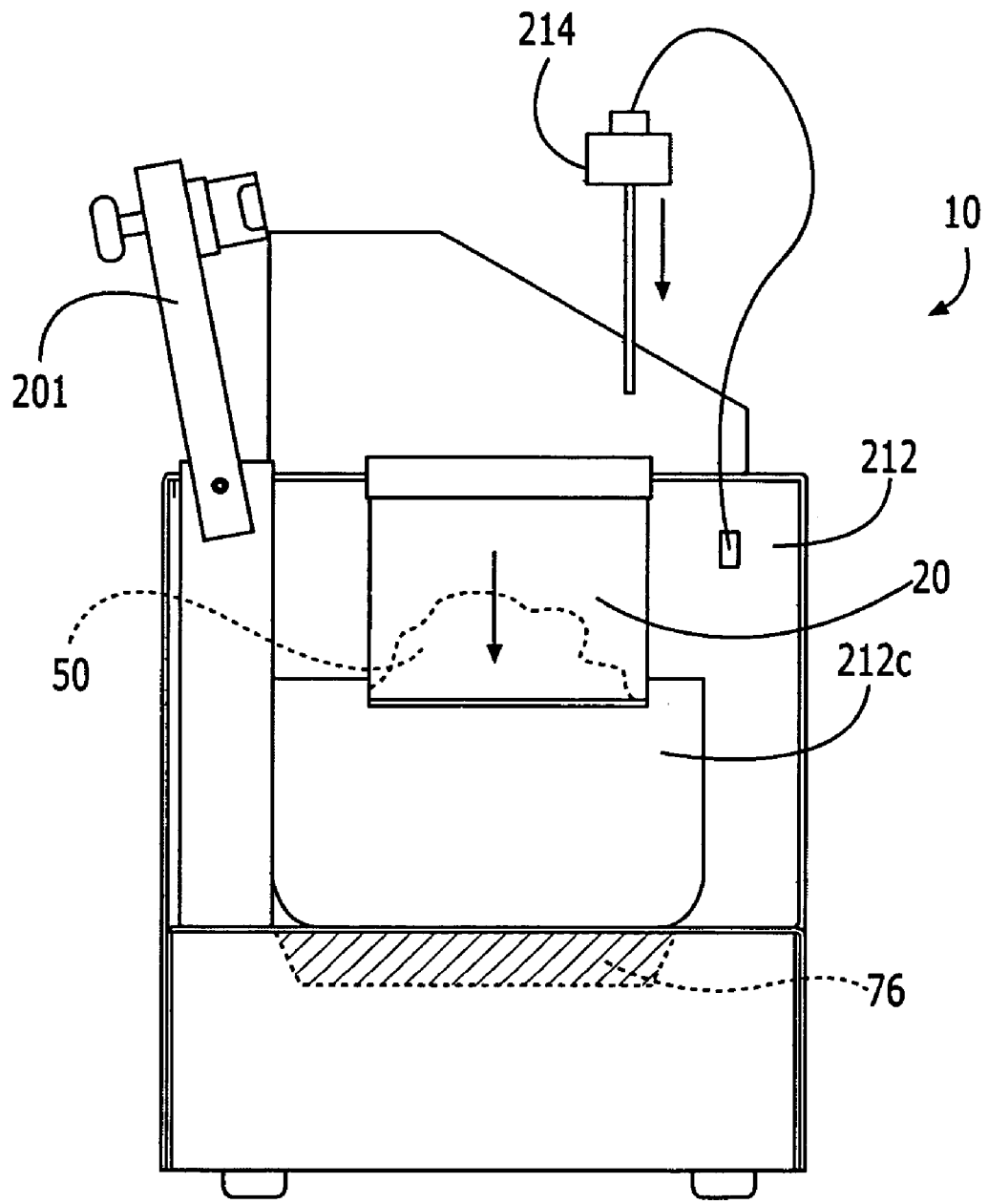
FIG. 11 is an end view of the system shown in FIG. 7A illustrating a configuration in which operations that can be carried out according to embodiments of the present invention.

FIG. 11 illustrates that the sample 50 in the container 20 can be loaded onto the housing 212. The photocell 208 (FIG. 7A, 8) detects the presence of the container 20 (with the sample 50). A temperature probe 214 can be inserted into the container into the sample 50. Other temperature sensors can be employed (and may be integrated into the container body) and need not be directly inserted into the sample. As such, a correlation can be used to estimate the temperature of the sample based on the indirect temperature. The temperature sensor 214 can be used to provide temperature data to the controller 75 (FIG. 4) to allow the controller to control the heat delivered to the sample during the evaluation via an integrated heater 76 (FIG. 7A).

Figure 12A:
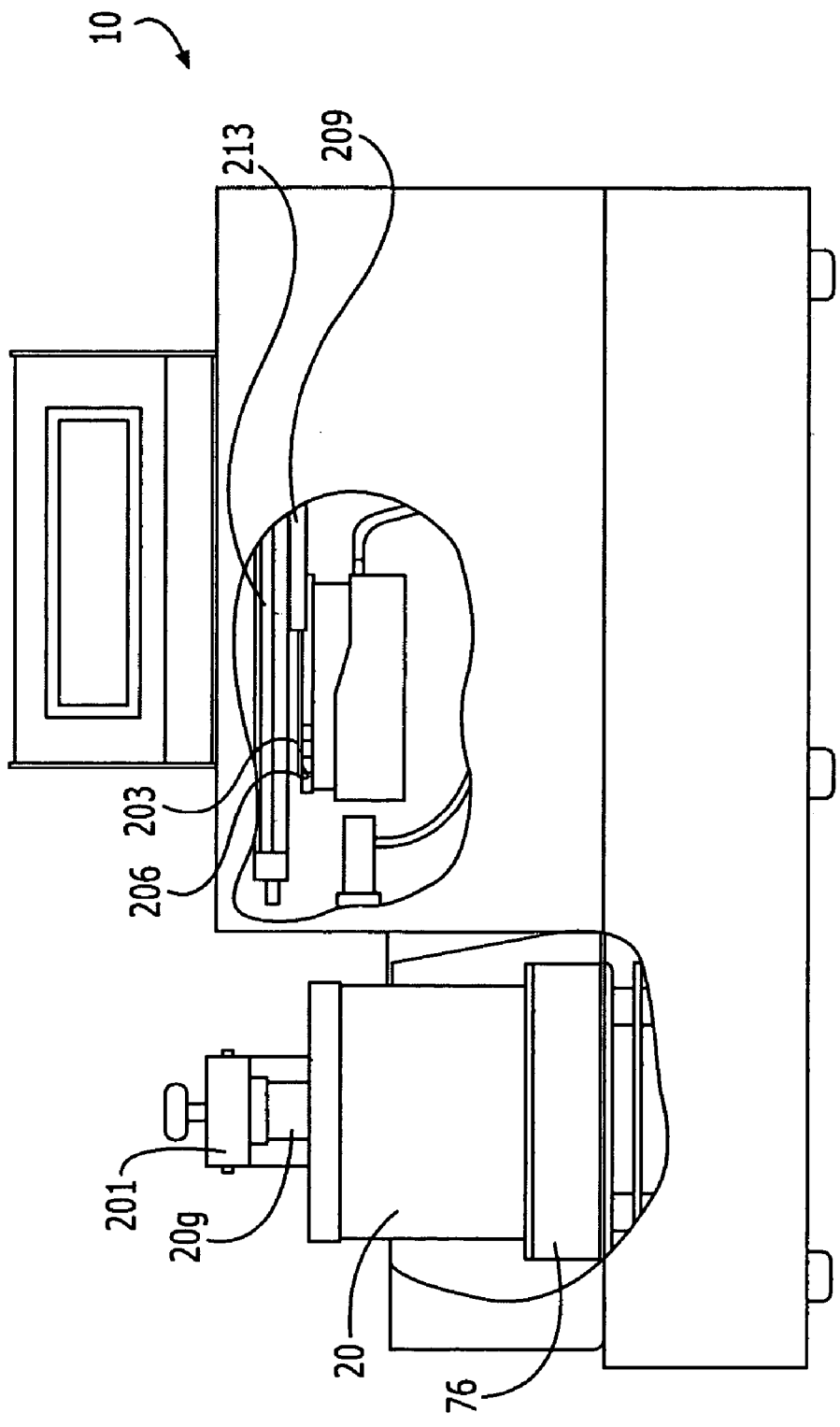
FIG. 12A is a partial cutaway front view of the device shown in FIG. 7A illustrating a sample container in position and the pH sensor residing in the housing according to embodiments of the present invention.
Figure 12B:
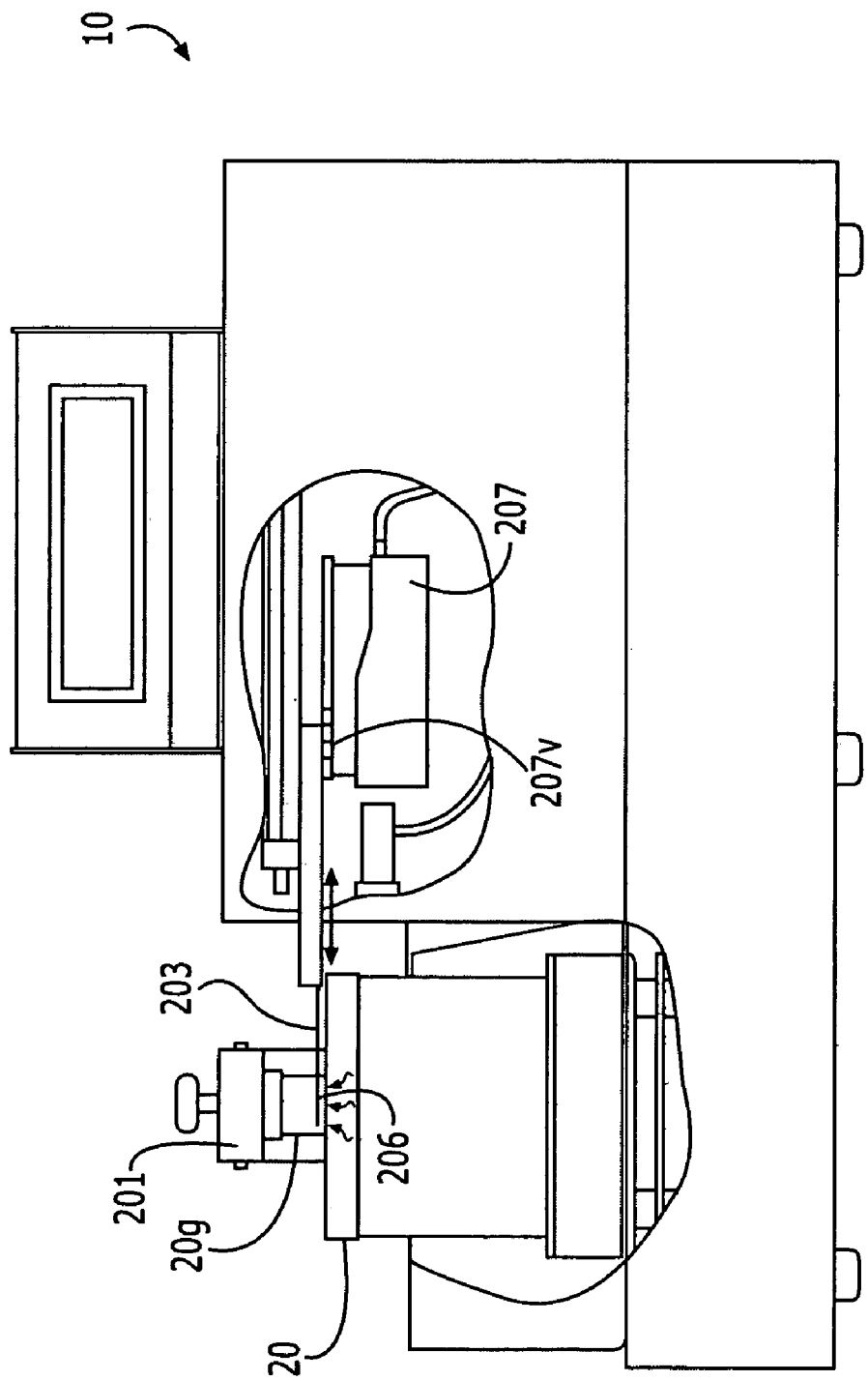
FIG. 12B is the same partial cutaway view shown in FIG. 12A but illustrating automated positioning of the sensor in proximity to the sample according to embodiments of the present invention.
Figure 12C:
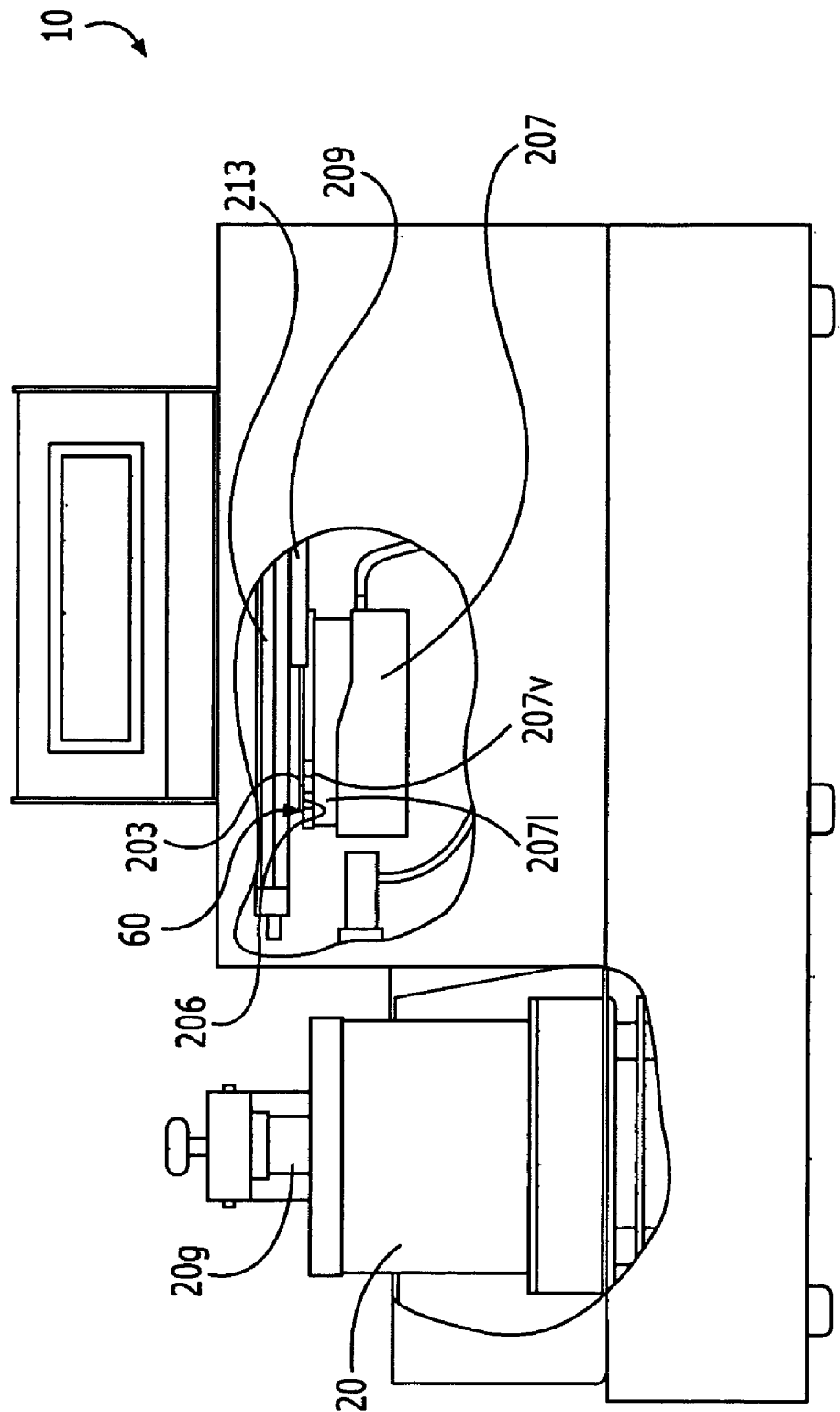
FIG. 12C is the same partial cutaway view shown in FIG. 12A but illustrating automated retraction of the sensor after sensing the vapor from the sample according to embodiments of the present invention.

FIG. 12A illustrates that the gas trap 20g can be assembled to the container 20 before the sensor 206 and frame member 203 are inserted therein (which can be held inside the housing 212 to inhibit premature exposure to the environmental fumes). The positive pressure in the housing 212 from the pressure provided by the cooling fan can inhibit entry of undesired exhaust fumes/vapors prior to initiation of the active sensing of the sample 50. FIG. 12B illustrates that, when the sample 50 is at a suitable temperature, the sensor 206 is inserted into the gas trap 20g above the aperture in the container 20 so that exhaust vapor emitted from the sample travels about the sensor paper 206. As shown in FIG. 12C, after a desired exposure time interval, the sensor 206 and frame member 203 retract into the housing 212 where the sensor 206 is aligned with the lens 207l and the photometer is activated and reads the sensor 206 at the optic viewing region 207v.

Figure 13:
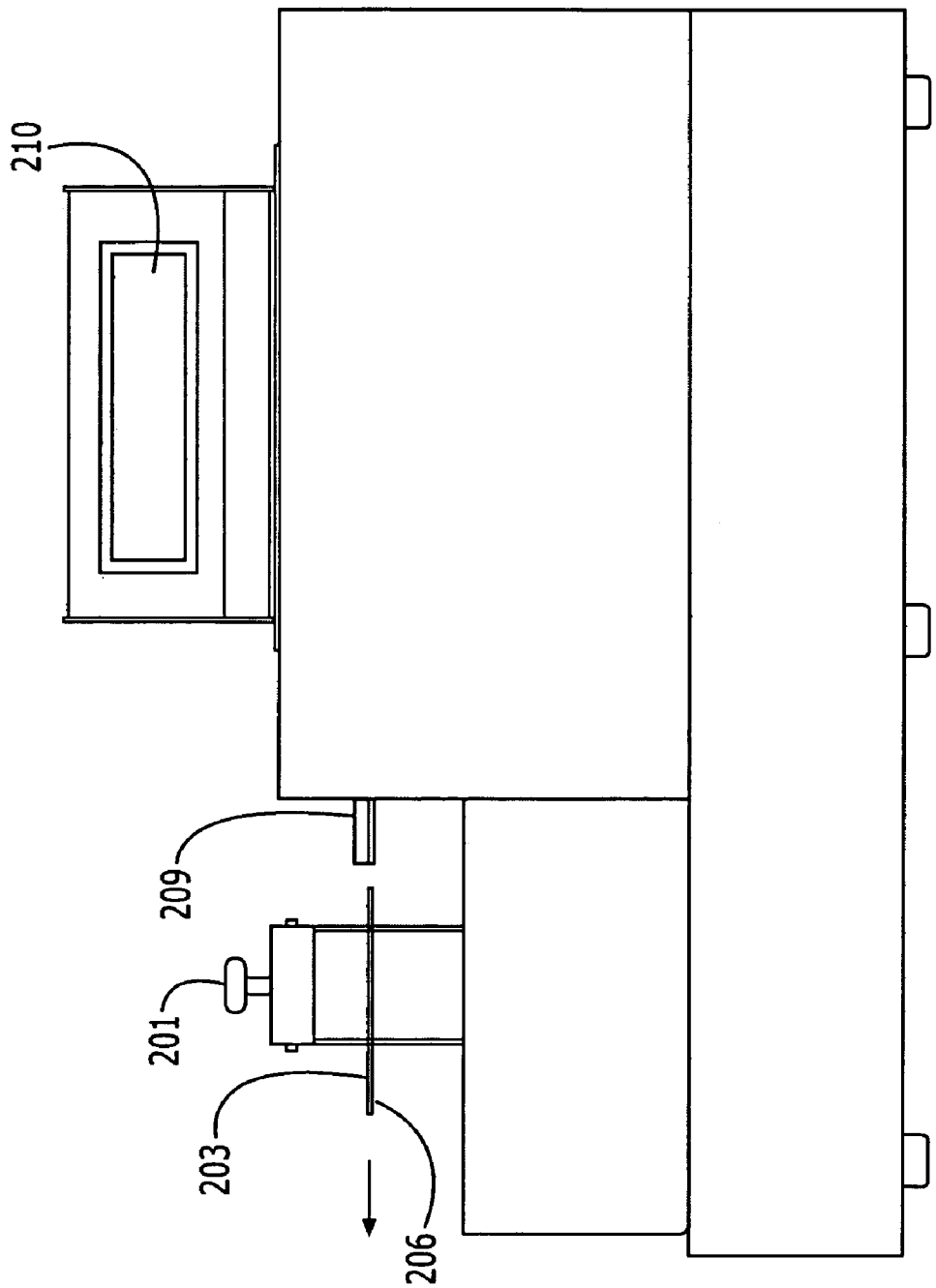
FIG. 13 is a front view of the system shown in FIG. 7A and illustrates that after the operation illustrated in FIG. 12C, the sample can be removed and the used (disposable) sensor discarded according to embodiments of the present invention.

FIG. 13 illustrates that after the reading is obtained, the container 20 with sample 50 is removed from the housing 212. The extension member 22e and the sensor 206 with frame member 203 may be discarded. Alternatively, the extension member 22e can be re-used (typically after cleaning to prevent any build-up from influencing the results of subsequent tests). In addition, the frame member 203 may be configured for re-use, and may, in particular embodiments, be configured as one of a plurality of such members that are rotated for use (such as in a carousel arrangement) and then retained on the positioning system 215 and cleansed as a part of maintenance and subsequent reloading with active sensors 206 (not shown).

In the embodiment shown in FIGS. 8–13, due to alkali property of anti-stripping chemicals, the interaction of the vapor with the sensor pH test paper will cause the paper go through color changes. The color can be measured using a spectrophotometer. The spectrophotometer can be configured to measure in the reflectance spectrum with a reflection-type meter with 45–0 geometry. Other embodiments may assess trasmissivity or absorption and the like. The reflectance embodiments can employ a configuration that illuminates or transmits a beam of visible light on the paper thorough a 45-degree angle, and measures the reflection light vertically (0 degree angle). The measurement generates a visible light spectra which extends from about 400 nm to 700 nm. Different colors have distinguishable visible light spectrum. Based on the spectrum distribution, an index can be created to relate the spectrum to the color on the test paper.

In certain embodiments, the apparatus or system can be configured so that it can be used to evaluate both types of samples (samples comprising asphalt binder materials without aggregates and asphalt mixtures with aggregates) for anti-stripping agents.

As noted above, the system, methods and apparatus may be used in different locations. When the apparatus is used in a laboratory environment and the asphalt sample is cold, the sample can be pre-heated in an oven to facilitate a volatilization process, so a phase change of anti-stripping chemical can take place. However, if the asphalt sample is hot at the time of collection, which is the case in the road pavement "hot-mix" site, and enough vapors emissions are generated from the sample, there will be no need to go through the pre-heating volatilization process. The vapor can be directly extracted in the device for analyzing. As such, the latter procedure is especially suitable for on site analysis of anti-stripping additive in a ready-mix asphalt pavement material. Usually, the asphalt pavement material is mixed in a plant and transported to a road site for pavement. Thus, when it arrives on the site, the material is still hot (i.e., a "hot-mix"). The apparatus can be used to assess directly the presence and the level of additives without preheating to cause it to go through a volatilization process.

The methods, systems, apparatus and computer programs contemplated by the present invention can be used in a qualitative way, to evaluate the presence of the anti-stripping chemicals in an asphalt material and/or in a quantitative manner to measure the level of the anti-stripping chemical in the asphalt material sample.

Although the spectrophotometer is shown in certain of the figures as integrated into the primary housing body, it will be appreciated that the spectrophotometer can be otherwise configured. For example, the spectrophotometer may be remotely positioned outside the primary housing and may be a stand-alone unit or configured to operate with the primary housing electronics.

Figure 14A:
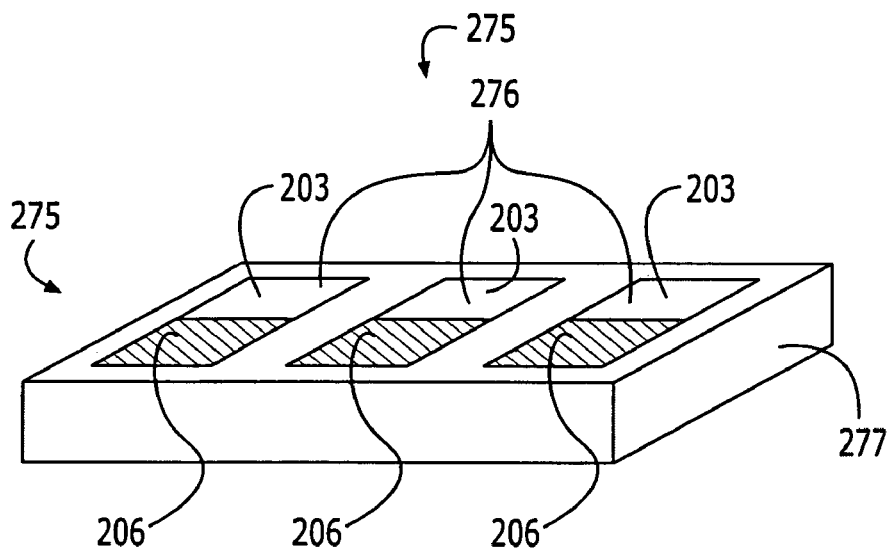
FIG. 14A is a schematic illustration of a packaged kit of single-use disposable sensor units.
Figure 14B:
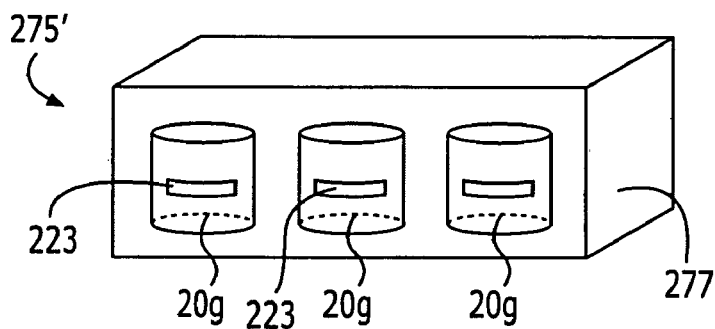
FIG. 14B is a schematic illustration of optionally disposable gas trap components configured to receive the sensor units shown in FIG. 14A according to embodiments of the present invention.

FIG. 14A illustrates that a kit 275 of disposable pH sensor units 276 can be provided that can provide easy loading units that can be releaseably attachable to the anti-stripping agent detection systems 10. The kit 275 includes a plurality of single-use disposable pH sensor units 276, each unit including a frame member 203 having opposing first and second primary surfaces and opposing first and second end portions and a pH paper such as litmus paper attached to a first end portion of at least one primary surface of the frame member 203. Each unit 276 may be covered in an elastomeric or other desired sealant and placed into a shipping container or package 277 for ease of handling and use and/or to protect the pH sensitive material from premature exposure. FIG. 14B illustrates that the kit 275' may alternatively and/or additionally comprise a plurality of discrete gas traps 20g, configured with ports 223 that allow the active sensors 206 of sensor units 276 to enter therein during operation. The gas traps 20g may be single or multi-use components.

Figure 15:
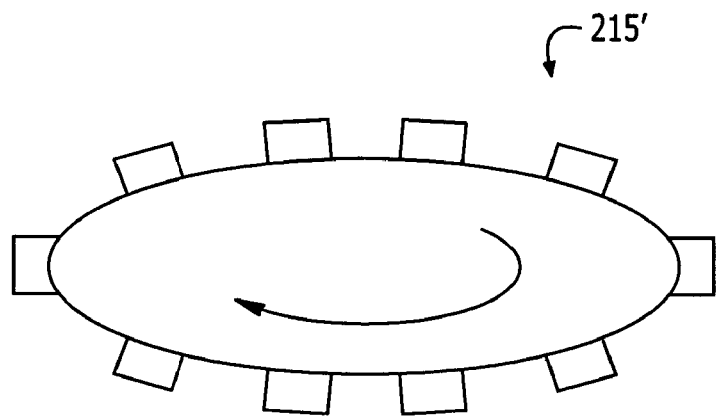
FIG. 15 is a schematic illustration of a configuration for a plurality of pre-loaded sensors in an automated advancing and use system according to embodiments of the present invention.
Figure 16:
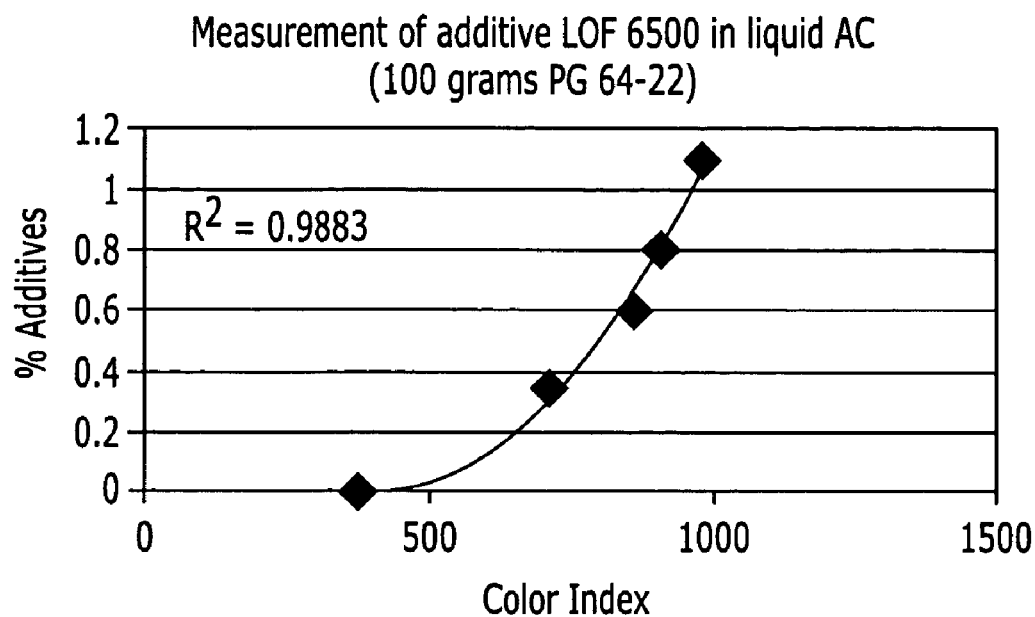
FIG. 16 is a graph of percentage of additives versus color index for LOF 6500 in liquid AC asphalt binder according to embodiments of the present invention.
Figure 17:
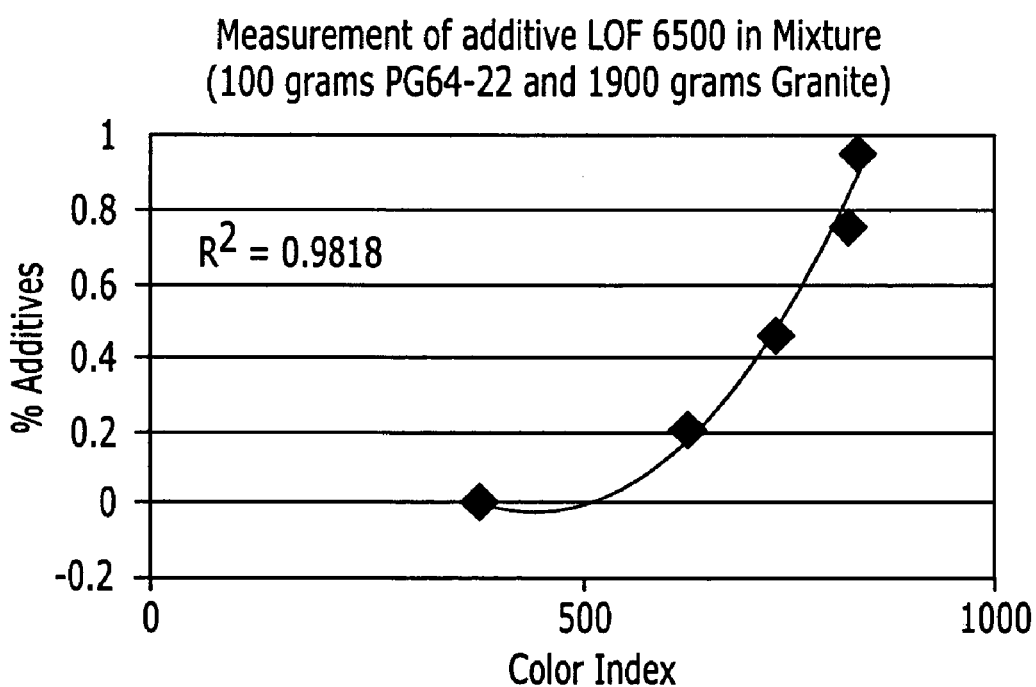
FIG. 17 is a graph of percentage of additives versus color index for LOF 6500 in mixture that can be used to calculate anti-stripping agent content according to embodiments of the present invention.
Figure 18:
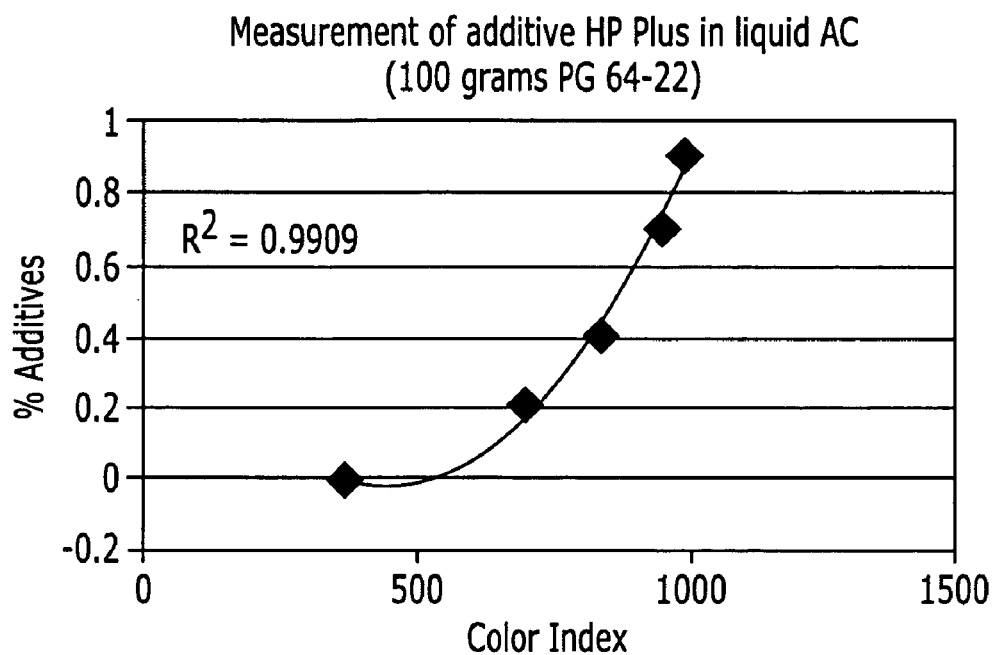
FIG. 18 is a graph of percentage of additives versus color index for HP Plus in liquid AC according to embodiments of the present invention.
Figure 19:
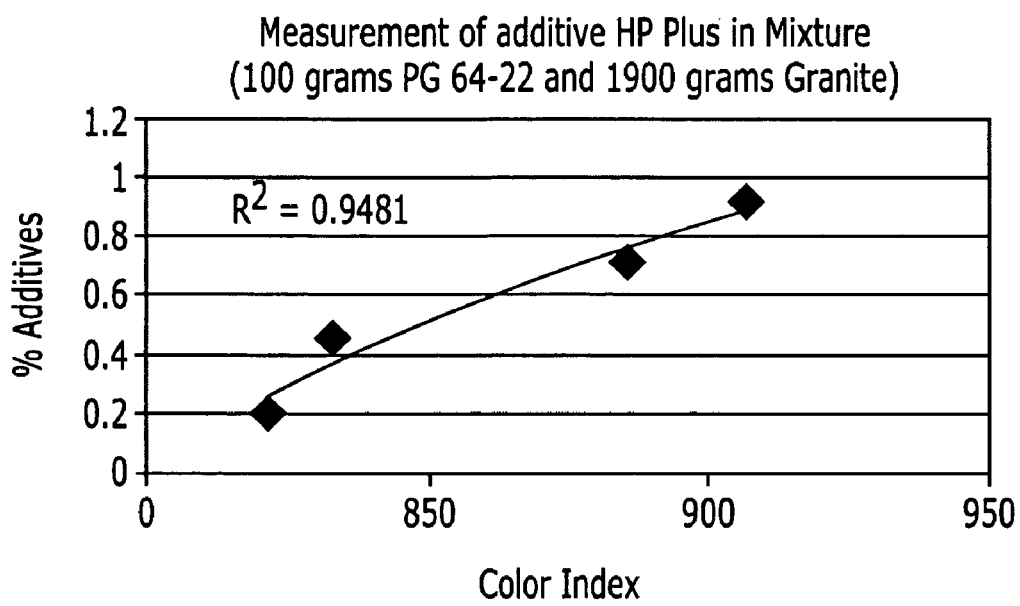
FIG. 19 is a graph of percentage of additives versus color index for HP Plus in mixture according to embodiments of the present invention.
Figure 20:
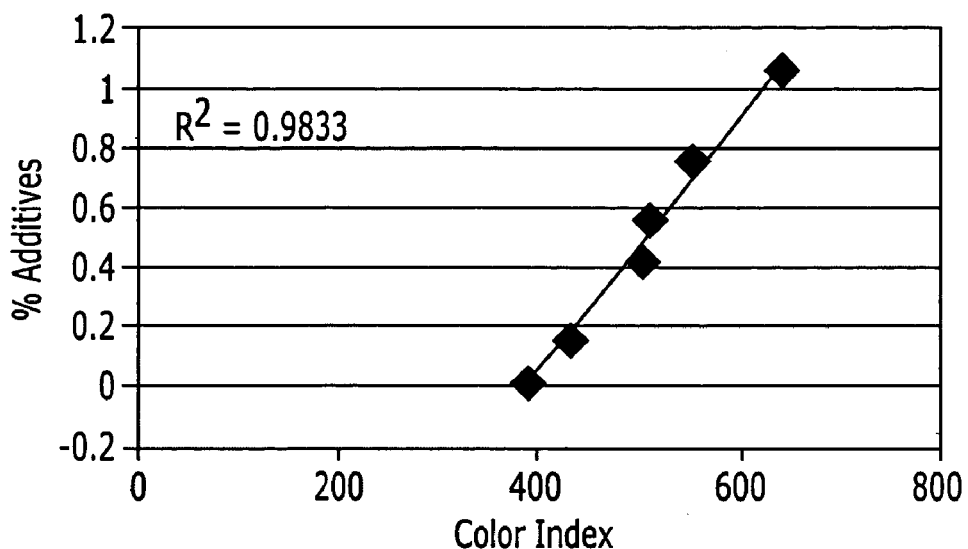
FIG. 20 is a graph of percentage of additives versus color index for MorLife 2200 in liquid AC according to embodiments of the present invention.
Figure 21:
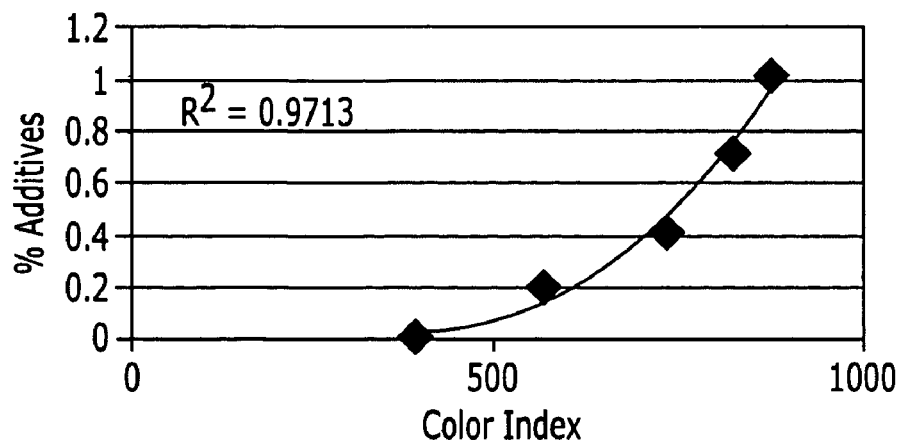
FIG. 21 is a graph of percentage of additives versus color index for MorLife 200 in mixture according to embodiments of the present invention.
Figure 22:
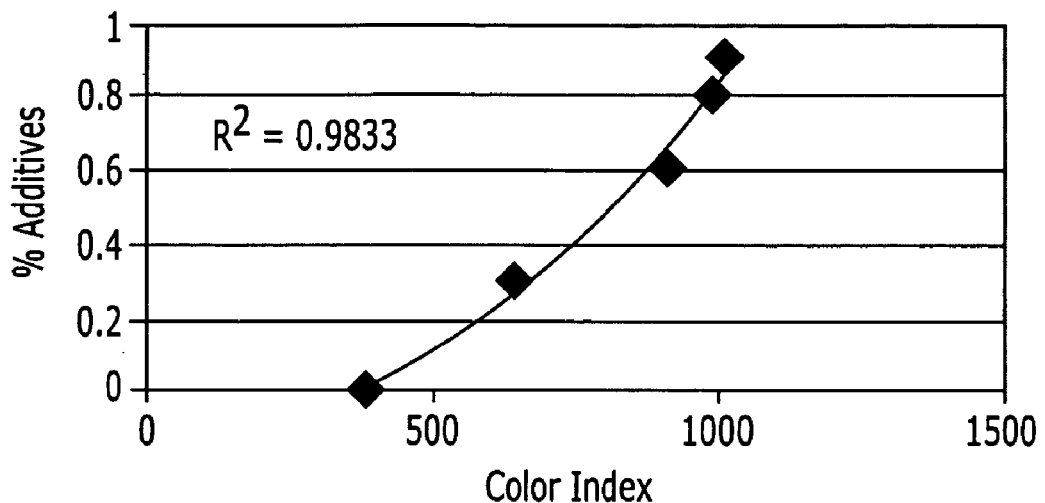
FIG. 22 is a graph of percentage of additives versus color index for MorLife 3300 in liquid AC according to embodiments of the present invention.
Figure 23:
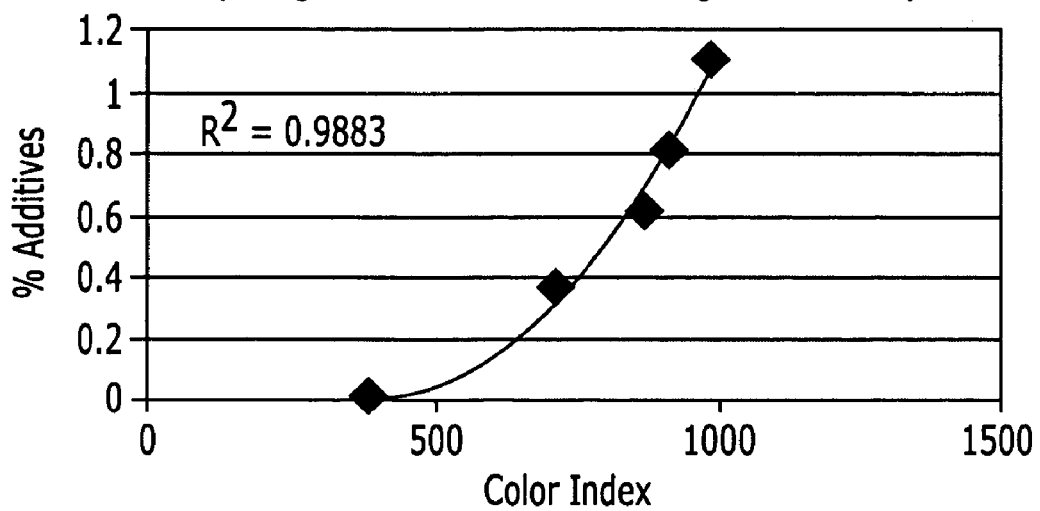
FIG. 23 is a graph of percentage of additives versus color index for MorLife 3300 in mixture according to embodiments of the present invention.

FIG. 15 illustrates one example of a track and positioning system 215' that can be pre-loaded with a plurality of sensor units 276 that can be serially and individually rotated and used at a desired time. The track and positioning system 215' may include a tray under the individual units that can be inserted into the apparatus and rotated to the use location. In other embodiments, the system 215' may grasp the end portions so that the units can be self-supporting.

The invention will now be illustrated with reference to certain examples which are included herein for the purposes of illustration only, and which are not intended to be limiting of the invention.

EXAMPLES

For quantitative measurements, a calibration standard or calculation with samples that have known amounts of chemicals can be established. Typically, at least three standard asphalt materials mixed with known amounts of antistripping additives are used in the calibration. In the method employed, the calibration was carried out to generate a relationship of color index versus percentage of additive in the material. Then, the calibration curve can be used to convert the color index from a measurement of an unknown mixture to the level of anti-stripping chemicals in the sample.

Due to differences in chemical compound of each brand of anti-stripping additives, an individual calibration may need to be performed for each type of additive. FIGS. 16 to 23 are examples of calibration curves of four common types of anti-stripping agents (additives) used in both binder (such as liquid AC) and mixture. The measurement precision as evaluated is slightly better in liquid AC than in a mixture.

While each additive brand may have a different calibration curve, the measurement sensitivity is good for all the additives tested, both in binder and asphalt mixture. The effect of different aggregate type and gradation may influence the test accuracy. Results have indicated that the vapor-based analysis method using the pH paper embodiment is capable of quantifying percentage of different types of anti-stripping additives in liquid and granite aggregate mixtures used in this study.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, when used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

The invention claimed is:

1. An automated method of analyzing at least one amine-based or acid-based anti-stripping agent in a sample comprising asphalt binder material, comprising:
   providing the sample comprising the asphalt binder material with the at least one amine-based or acid-based anti-stripping agent;
   heating and/or preheating the sample to a sufficient temperature for a sufficient time to generate an exhaust vapor;
   capturing the exhaust vapor emitted from the sample;
   exposing a pH sensor to the captured exhaust vapor;
   automatically detecting color of the pH sensor exposed to the captured exhaust vapor;
   automatically comparing the detected color with reference calibration data of colors versus levels of anti-stripping agent associated with known reference samples; and
   automatically determining the presence and/or level of the at least one amine-based or acid-based anti-stripping agent in the sample based on the detected color of the pH-sensor and the reference calibration data.

2. A method according to claim 1, wherein the determining step is carried out to determine the concentration level of the at least one amine-based or acid-based anti-stripping agent present in the sample.

3. A method according to claim 2, wherein the capturing, detecting and determining steps are carried out in situ at a field or refinery site.

4. A method according to claim 2, wherein the capturing, detecting and determining steps are carried out at a testing laboratory.

5. A method according to claim 1, wherein the detecting step is carried out in about 10 minutes or less after the sample is heated to a predetermined temperature for a predetermined time.

6. A method according to claim 1, further comprising:
   positioning the sample in an enclosed chamber having the pH sensor disposed at an upper portion thereof so that the pH sensor resides above the material sample; and
   directing the captured exhaust vapor to flow upwardly in the chamber toward the pH sensor.

7. A method according to claim 1, wherein the providing step is carried out by providing the sample in a predetermined weight, the method further comprising:
   placing the sample in a container having an enclosed chamber configured with a predetermined volume; and
   exposing the pH sensor to the captured exhaust vapor in the container for a predetermined time while the sample is at a temperature that is at or above a predetermined temperature.

8. A method according to claim 7, further comprising heating the sample to a predetermined temperature before placing the sample into the container.

9. A method according to claim 8, further comprising heating the sample while the sample is held in the container; and monitoring the temperature of the sample in the container before exposing the pH sensor to the vapor.

10. A method according to claim 1, wherein the sample is obtained from a hot-mix batch of asphalt mixture comprising the at least one amine-based or acid-based anti-stripping agent at a field site.

11. A method according to claim 1, wherein the sample is obtained from an asphalt binder material comprising the at least one amine-based or acid-based anti-stripping agent at a refinery site.

12. A method according to claim 1, wherein the pH sensor detecting step comprises litmus paper that generates a graduated detectable color alteration when exposed to the exhaust vapor.

13. A method according to claim 1, wherein the determining step comprises automatically calculating the concentration of the anti-stripping agent in tile sample based on the color of the pH sensor after exposure to the exhaust gas using the reference calibration data, and wherein the reference calibration data comprises color index data, a respective color index corresponding to different percentages and a corresponding color value of a predetermined combination of a selected material binder and anti-stripping agent, and wherein the determining step uses color index data to calculate a level of anti-stripping agent in the sample.

14. A method according to claim 13, wherein the detecting step is carried out using a spectrophotometer that measures color change in the reflectance spectrum of the wavelength between about 400–700 nm in the visible range and comparing the measured color to a color index appropriate for the sample undergoing analysis.

15. An automated method of analyzing a volatile anti-stripping agent in a sample of asphalt binder material, comprising:
obtaining the sample comprising the asphalt binder material with the volatile anti-stripping agent;
heating and/or preheating the sample to a sufficient temperature for a sufficient time to generate an exhaust vapor from the volatile anti-stripping agent;
exposing an optical sensor to the exhaust vapor from the volatile anti-stripping agent in the sample;
detecting an optical property of the exhaust vapor;
automatically comparing the detected optical property of the exhaust vapor to reference calibration data obtained with the optical sensor for known reference samples; and
automatically determining at least one of the presence, absence or level of the volatile anti-stripping agent in the sample based on the comparing step.

16. A method according to claim 15, wherein the optical property comprises at least one of: color, reflectance, transmittance, and/or absorption.

17. A method according to claim 15, wherein the optical sensor is a pH sensor that is configured to change color in response to exposure to an amine or acid based volatile anti-stripping agent during the exposing step, and wherein the optical property is color.

18. A method according to claim 17, wherein the exposing step comprises controllably heating the sample to a predetermined temperate for a predetermined time and exposing the pH sensor to the exhaust vapor, and wherein the comparing and detecting steps comprise automatically comparing the color of the pH sensor with the reference calibration data, and automatically calculating the level of the anti-stripping agent in the sample using the reference data for the known samples.

19. A method according to claim 18, further comprising protecting the pH sensor from premature exposure to the vapor prior to the exposing step.

20. A meted according to claim 18, wherein the predetermined time is about five minutes.

21. A method according to claim 18, the method further comprising heating the sample so that the sample predetermined temperature is at least about 280° F. as measured in an internal location in a volume of the sample for the predetermined time before the exposing step.

22. A method according to claim 18, the method further comprising electronically controlling the time the sample is at or above the predetermined temperature before automatically translating the pH sensor into position to carry out the exposing step.

23. A method according to claim 22, further comprising automatically retracting the pH sensor away from exposing to the vapor and into position with an optical spectrophotometer, and wherein the comparing step comprises automatically obtaining an optical spectrum of the pH sensor using the optical spectrophotometer and comparing the spectrum with spectra of the reference samples.

24. A method according to claim 22, wherein the obtaining step comprises providing a defined sample weight that generates a defined vapor volume prior to the exposing step.

25. A method according to claim 17, wherein the reference calibration data comprises data associated with a color index versus percentage of the anti-stripping agent for a plurality of different formulations of anti-stripping agents including formulations with liquid asphalt concrete and formulations with aggregate and liquid asphalt concrete.

26. A method according to claim 17, wherein the providing step comprises
generating an electronic reference calibration data library of pH sensor data corresponding to the optical property of a plurality of known selected combinations of material binders and anti-stripping agents.

27. A method according to claim 26, wherein the reference calibration data of pH sensor data comprises pH sensor color associated with the amine-based or acid-based anti-stripping agent for the plurality of known selected combinations of binders and anti-stripping agents.

28. A method according to claim 27, wherein the reference calibration data of pH sensor color data is generated using a plurality of electronic color index calibration curves, each curve corresponding to different percentages and corresponding color value of a predetermined combination of a selected material binder and anti-stripping agent, and wherein the detecting step uses data from the color index calibration curves to calculate a level of anti-stripping agent in the sample.

29. A method according to claim 17, further comprising capturing exhaust vapor and directing the captured exhaust vapor to travel through a selected medium, wherein the detecting step comprises sensing the medium for a color change in the exposed pH sensor to determine the level of anti-stripping agent in the sample.

30. A method according to claim 29, wherein the selected medium is liquid.

31. A method according to claim 29, wherein the selected medium comprises deionized water.

32. A method according to claim 17, wherein the pH sensor comprises litmus paper.

33. A method according to claim 17, wherein the selected optically detectable property is color, and wherein the comparing step comprises automatically operating a spectrophotometer that measures color change in a reflectance spectrum of a wavelength of a whole visible range to measure the color of the exposed pH sensor.

34. A method according to claim 15, wherein the obtaining step is carried out by providing the sample in a predetermined quantity.

35. A method according to claim 15, further comprising positioning the obtained sample in an enclosed evaluation chamber, the evaluation chamber having an electronically translatable sensor operatively associated therewith, so that, in operation, the sensor is controllably translated into position in fluid communication with the vapor during the exposing step.

36. A method according to claim 15, wherein the obtained sample is a hot-mix sample comprising asphalt binder material, at least one anti-stripping agent, and aggregates.

37. A method according to claim 36, wherein the sample is sized at between about 1000–4000 grams.

38. A method according to claim 15, wherein the obtained sample is an asphalt binder that is devoid of aggregates.

39. A method according to claim 38, wherein the sample is devoid of aggregates and is sized at between about 50–1000 grams.

40. A method of analyzing a volatile acidic or basic anti-stripping agent content of an asphalt binder material sample, comprising:
heating an asphalt material sample comprising the volatile acidic or basic anti-stripping agent to generate exhaust vapor for a predetermined time at or above a predetermined temperature;

placing a pH sensor in fluid communication with the exhaust vapor to expose the pH sensor to the exhaust vapor;

automatically detecting a color associated with the exposed pH sensor; and automatically calculating a level of the anti-stripping agent in the sample by automatically comparing the detected color to electronic reference calibration color data.

41. A method according to claim 40, wherein the pH sensor comprises litmus paper, and wherein the color of the litmus paper is detected by a spectrophotometer, and wherein the calculating step converts color of the litmus paper in the visible light spectrum to concentration of the acidic or basic anti-stripping agent in the sample using the reference calibration color data.

42. A method according to claim 41, wherein the anti-stripping agent is an amine or acid based anti-stripping agent, and wherein the acidic or basic detecting step comprises automatically operating the spectrophotometer to detect the color of the exposed litmus paper.

* * * * *

UNITED STATES PATENT AND TRADEMARK OFFICE
CERTIFICATE OF CORRECTION

PATENT NO. : 7,098,034 B2
APPLICATION NO. : 10/327833
DATED : August 29, 2006
INVENTOR(S) : He et al.

It is certified that error appears in the above-identified patent and that said Letters Patent is hereby corrected as shown below:

Column 20,
Line 53 should read -- centration of the anti-stripping agent in the sample based on --

Signed and Sealed this

Second Day of January, 2007

JON W. DUDAS
*Director of the United States Patent and Trademark Office*